(12) United States Patent
Bow et al.

(10) Patent No.: US 12,070,533 B2
(45) Date of Patent: Aug. 27, 2024

(54) METAL ALLOY AND MEDICAL DEVICE CONTAINING SAME

(71) Applicant: Tam Christine Thompson-Steckel, Paisley (GB)

(72) Inventors: David Russell Bow, Glasgow (GB); Calum Bruce Macleod, Glasgow (GB); Jeffrey Jump, Prangins (CH)

(73) Assignee: Tam Christine Thompson-Steckel, Paisley (GB)

( * ) Notice: Subject to any disclaimer, the term of this patent is extended or adjusted under 35 U.S.C. 154(b) by 553 days.

(21) Appl. No.: 16/642,730

(22) PCT Filed: Aug. 30, 2018

(86) PCT No.: PCT/GB2018/052459
§ 371 (c)(1),
(2) Date: Feb. 27, 2020

(87) PCT Pub. No.: WO2019/043394
PCT Pub. Date: Mar. 7, 2019

(65) Prior Publication Data
US 2020/0376172 A1 Dec. 3, 2020

(30) Foreign Application Priority Data

Aug. 30, 2017 (GB) ..................................... 1713907

(51) Int. Cl.
*A61F 2/88* (2006.01)
*A61F 2/90* (2013.01)
(Continued)

(52) U.S. Cl.
CPC .............. *A61L 31/022* (2013.01); *A61F 2/88* (2013.01); *A61F 2/90* (2013.01); *A61L 31/06* (2013.01);
(Continued)

(58) Field of Classification Search
CPC .... C22C 23/06; A61F 2/88; A61F 2230/0091; A61F 2210/0004; A61F 2250/0037; A61F 2002/825; A61L 31/022
(Continued)

(56) References Cited

U.S. PATENT DOCUMENTS 6,287,332 B1    9/2001   Bolz et al.
6,485,510 B1 *   11/2002   Camrud .................... A61F 2/88
                                                              623/1.16
(Continued)

FOREIGN PATENT DOCUMENTS

CN         1743486 A    3/2006
CN      101285143 A   10/2008
(Continued)

OTHER PUBLICATIONS

Abstract of WO2009157164 (Year: 2009).*
(Continued)

*Primary Examiner* — Brian E Pellegrino
(74) *Attorney, Agent, or Firm* — Knobbe, Martens, Olson & Bear, LLP

(57) ABSTRACT

There is described a bioresorbable metal alloy which is particularly suitable for the formation of bioresorbable medical devices, for example stents. The metal alloy essentially comprises 3.2 to 4.8% by weight lithium, 0.5 to 2.0% by weight yttrium; and the balance being magnesium, in addition to any trace elements. The metal alloy can be drawn into a wire which can be shaped into a stent scaffold. The stent can be produced using one or more stent scaffolds together with one or more bioresorbable polymer connectors, for example formed from PLGA.

31 Claims, 10 Drawing Sheets

(51) Int. Cl.
*A61L 31/02* (2006.01)
*A61L 31/06* (2006.01)
*A61L 31/10* (2006.01)
*A61L 31/14* (2006.01)
*B33Y 80/00* (2015.01)
*C08G 63/08* (2006.01)
*C09D 5/00* (2006.01)
*C09D 167/04* (2006.01)
*C22C 23/00* (2006.01)
*A61F 2/82* (2013.01)

(52) U.S. Cl.
CPC ............ *A61L 31/10* (2013.01); *A61L 31/148* (2013.01); *B33Y 80/00* (2014.12); *C08G 63/08* (2013.01); *C09D 5/00* (2013.01); *C09D 167/04* (2013.01); *C22C 23/00* (2013.01); *A61F 2002/825* (2013.01); *A61F 2210/0004* (2013.01); *A61F 2230/0091* (2013.01); *A61F 2240/001* (2013.01); *A61F 2250/0067* (2013.01)

(58) Field of Classification Search
USPC ........................................................ 420/402
See application file for complete search history.

(56) References Cited

U.S. PATENT DOCUMENTS

| | | | |
|---|---|---|---|
| 8,888,841 | B2 | 11/2014 | Pandelidis et al. |
| 8,900,619 | B2 | 12/2014 | Ranade et al. |
| 8,986,369 | B2 | 3/2015 | Steckel et al. |
| 2004/0106975 | A1* | 6/2004 | Solovay ............... A61F 2/91 623/1.11 |
| 2012/0172970 | A1* | 7/2012 | Cottone, Jr. ........... A61L 31/10 623/1.42 |
| 2013/0090741 | A1 | 4/2013 | Guo et al. |
| 2015/0272753 | A1 | 10/2015 | Steckel et al. |
| 2019/0153570 | A1 | 5/2019 | Zhou et al. |

FOREIGN PATENT DOCUMENTS

| | | | | |
|---|---|---|---|---|
| CN | 10239164 | | 3/2012 | |
| CN | 102392164 | | 3/2012 | |
| CN | 103643096 | A | 3/2014 | |
| CN | 105845884 | A | 8/2016 | |
| CN | 106521274 | | 3/2017 | |
| DE | 102016007176 | A1 * | 1/2017 | ......... A61L 31/022 |
| EP | 0221570 | | 5/1987 | |
| EP | 565251 | A1 * | 10/1993 | ............... A61F 2/88 |
| EP | 910998 | A2 * | 4/1999 | ............... A61F 2/91 |
| EP | 1036551 | A2 * | 9/2000 | ............... A61F 2/88 |
| JP | H0625789 | | 2/1994 | |
| JP | H0649576 | | 2/1994 | |
| JP | 2003/226929 | | 8/2003 | |
| WO | WO-2009157164 | A1 * | 12/2009 | ............... A61F 2/88 |
| WO | WO 2014/197781 | | 12/2014 | |
| WO | WO-2015007435 | A1 * | 1/2015 | ............. A61F 2/915 |

OTHER PUBLICATIONS

Translation of DE 102016007176 (Year: 2017).*
Patent Cooperation Treaty, International Search Report and Written Opinion, Application No. PCT/GB2018/052459, dated Dec. 20, 2018, in 8 pages.

* cited by examiner

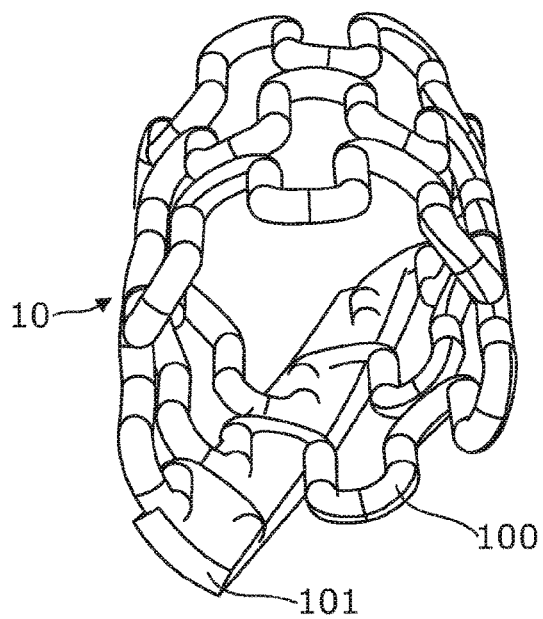
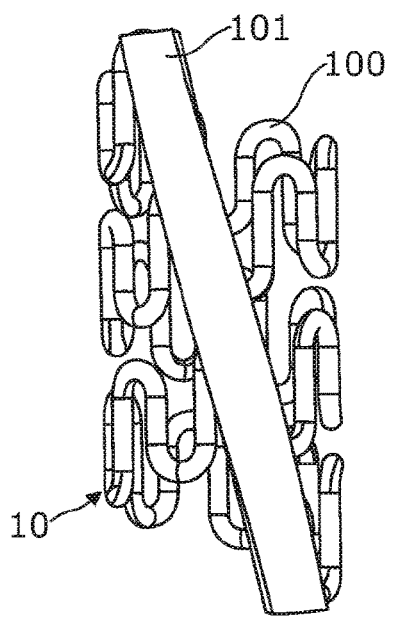
Figure 16A    Figure 16B
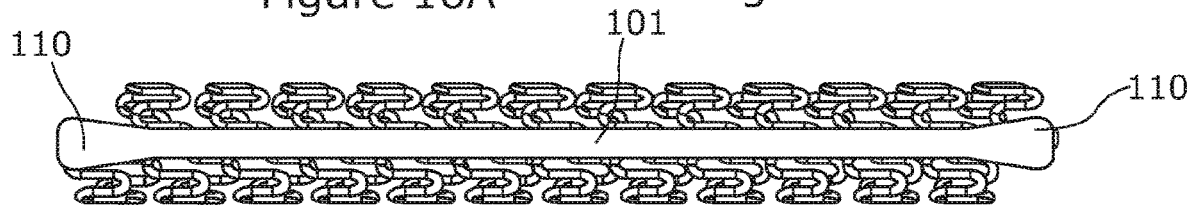
Figure 17
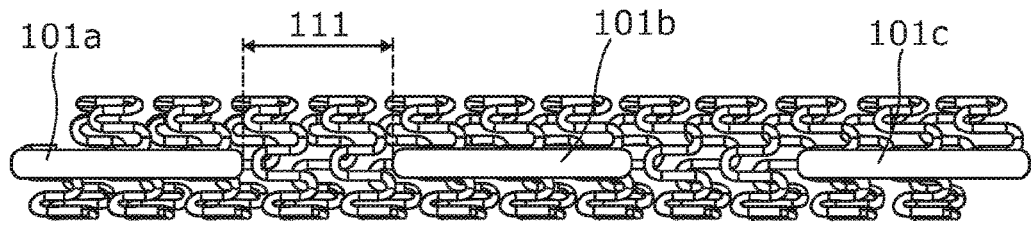
Figure 18
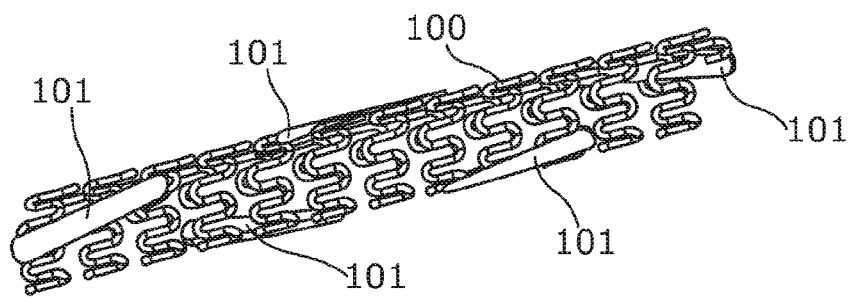
Figure 19

METAL ALLOY AND MEDICAL DEVICE CONTAINING SAME

TECHNICAL FIELD

The present invention relates to a novel alloy suitable for use in implantable medical devices in order to treat diseased or damaged tissue, and in particular for use in temporary medical devices which are resorbed by the body over time. The present invention further relates to novel resorbable medical devices, particularly devices such as stents which can be used to ameliorate the progressive narrowing of natural body lumens, for example arterial blood vessels.

BACKGROUND TO THE INVENTION

Arteriosclerosis refers to the narrowing of arterial blood vessels that results in ischemia to vital organs and tissue. The reduction of blood supply translates into symptoms such as angina on exertion for narrowed coronary arteries of the heart, to lower limb amputation with Critical Limb Ischemia for narrowing of the major arteries of the upper and lower leg. In addition to vascular disease, other bodily structures such as the esophagus, bile duct, ureter and trachea can become narrowed or blocked due to disease, trauma, or congenital defects.

Since the 1980's such narrowing of vessel lumen have been treatable by minimally invasive, catheter-based medical device technologies that expand the narrowed vessel lumen to its native diameter. The original catheter-based or interventional therapy was balloon angioplasty, where a high-pressure balloon at the end of a long flexible catheter was inserted into the narrowed vessel and inflated to pressures typically greater than 810 kPa (8 atm). The balloon pressure would often dissect the intima of the vessel allowing the central lumen to be expanded to near to its native diameter. This technology was widely adopted for both coronary and peripheral interventions, as well as other luminal structures within the body.

Two complications of balloon angioplasty are acute obstruction of the vessel due to either vessel spasm and/or a dissected intimal flap, and late restenosis due to neointimal tissue proliferation initiated by the mechanical injury. The issue of acute occlusion due to spasm or intimal flap was remedied by the development of the stent which is an expandable cage that permanently supports the vessel lumen. Palmaz describes a laser cut, slotted hypo-tube design of stent in EP0221570A. Whilst the advent of the stent provided for an acute mechanical support of the vessel lumen, a significant number of patients experienced a long term re-narrowing of the vessel, termed restenosis. During ballooning and stent placement, the vessel's inner layer, the intima, is often dissected due to the overexpansion of the stent. Smooth muscles cells from the vessel intima can migrate and proliferate into the lumen, resulting in scar tissue or "neointimal hyperplasia" that narrows the vessel lumen interior to the permanent stent.

The use of local delivery of potent anti-proliferative drugs from the surface of permanent stents was a significant development to reduce the incidence of restenosis. Drugs such as sirolimus and paclitaxel delivered post-implantation from controlled release formulations over a period of weeks to months have been conclusively shown to inhibit the smooth muscle cell migration and proliferation that results from vessel injury during stenting.

However, one persistent complication from permanent stents is Late Stent Thrombosis (LST), where an obstructive thrombosis or clot is formed within the stent, generally 1 year post-implantation or later, and typically after dual antiplatelet therapy has ceased. There are several factors that are believed to contribute to LST. One factor is that a permanent stent essentially eliminates the normal peristaltic motion of the vessel due to the un-yielding mechanical properties of the stent within the vessel. Another factor is that the polymers used to deliver the anti-proliferative drugs are not ideal for full vessel healing and inhibit the formation of a fully functioning endothelium that it is the primary mechanism for preventing thrombus formation. Stent struts from conventional stents that are mal-apposed to the vessel wall also create an environment favourable to the formation of late in-stent thrombosis.

One approach to eliminate these chronic complications from permanent stents is to treat the diseased vessel with a temporary scaffold that provides acute mechanical support to the re-opened but mechanically compromised vessel, optionally delivers an anti-proliferative drug, and is then safely resorbed by the body, leaving a remodeled native vessel without physical impediments to endothelization or to restored local peristaltic motion.

There have been several approaches to developing a fully bioresorbable vascular scaffold (BVS). An early approach was to use expandable designs made from poly-L-lactic acid (PLLA) polymer. Whereas this approach leverages materials with known biologic safety, stents formed from PLLA exhibit poor mechanical properties relative to conventional stent materials such as 316 LVM Stainless Steel, Cobalt Chromium, or Nitinol in terms of significantly lower Young Modulus, tensile strength, and ability to plastically deform. Some of the consequences of the limited mechanical properties of PLLA include a very limited range of expansion for a given stent design which provides poor strut-wall apposition, particularly when the stent is deployed into tapered vessels or any non-cylindrical vessel due to plaque, angulation, tortuosity, etc. The low mechanical properties need to be compensated for with larger, bulkier struts that are not able to embed into the vessel wall in the same way as thinner metal struts, resulting in a condition that is believed to favour formation of LST.

Another major issue with PLLA based stents is the very long absorption time, with fragments of polymer being retained in the vessel wall for over 2 years and an increased rate of thrombotic events 3 years post procedure.

Another attempt to develop a BVS was the introduction of so-called bioresorbable metals such as magnesium alloys (as described in U.S. Pat. No. 6,287,332). These stents behave like traditional stainless steel stents in terms of their ability to achieve strut embedding and strut-wall apposition. The magnesium alloys resorb through an oxidation of the metal, followed by solubilization and metabolization of the metal oxides, metal halides, etc. that are formed in vivo. However bioresorbable magnesium alloy stents are known to suffer from early strut fracture coupled with long absorption times, resulting in suboptimal clinical outcomes. The long absorption time is associated with the insoluble, heavy metal (rare earth) elements used in the alloy, which prolongs the foreign body reaction.

Thus U.S. Pat. No. 6,287,332 suggests addition of rare earth metals to magnesium alloys to improve yield strength, but the poor solubility of these metals in physiologic aqueous fluids negatively extend absorption times.

U.S. Pat. Nos. 8,888,841 and 8,986,369 teach Mg—Li alloys without any rare earth elements, but these alloys exhibit a columnar microstructure, and therefore exhibit poor mechanical properties. U.S. Pat. No. 8,888,841 describes an Mg—Li alloy which is substantially free of rare earth elements, as part of a uni-directionally solidified or single crystal-like microstructure. This alloy should have improved biological safety relative to alloys containing rare earth elements, but may not have the mechanical strength to resist recoil in normal or calcified vessels. The alloy described in U.S. Pat. No. 8,888,841 also suffers from limitations of the columnar microstructure regarding timing and uniformity of the metal's disintegration and resorption. The end-stage degradation for bioresorbable implants are key to their biocompatibility, with many demonstrating late profound events associated with a final spike in concentration of degradants that is highly inflammatory.

SUMMARY OF THE INVENTION

It is an object of the present invention to provide a biocompatible, bioresorbable metal alloy which has sufficient mechanical strength to be useful in medical devices, for example load bearing medical devices, for example stents, and particularly in terms of decreased strut fracture, and which has a suitable bioresorption profile, for example which is fully absorbed in a period of less than one year thereby allowing the host vessel to fully heal and remodel.

The present invention notes that yttrium and its salts have a sufficiently high solubility in aqueous fluids to be absorbed and metabolized from the soft tissue implant site, whilst also allowing sufficient improvement in yield strength when incorporated into an alloy. Thus it is an object of the present invention to provide biocompatible, bioresorbable metal alloy containing yttrium.

It is further an object of the present invention to provide a biocompatible, bioresorbable metal alloy which has fine, poly-grain microstructures.

It is further an object of the present invention to provide a medical device, such as a stent, comprising the biocompatible, bioresorbable metal alloy of the invention.

It is further an object of the present invention to provide a stent formed from the biocompatible, bioresorbable metal alloy of the invention, together with at least one bioresorbable polymer element.

BRIEF DESCRIPTION OF THE FIGURES

FIG. 16A shows an alternative embodiment of a stent according to the present invention in which the connector is orientated to have an alternative helical direction.

FIG. 16B shows the embodiment of FIG. 16A when viewed from the side.

FIG. 17 shows a further embodiment of a stent according to the present invention in which the connector member is enlarged at each end.

FIG. 18 shows a further embodiment of a stent according to the present invention in which the connector member is provided in discontinuous lengths.

FIG. 19 shows another embodiment of a stent according to the present invention in which the connector member is discontinuous and has a helical orientation.

DETAILED DESCRIPTION OF THE INVENTION

Figure 1:
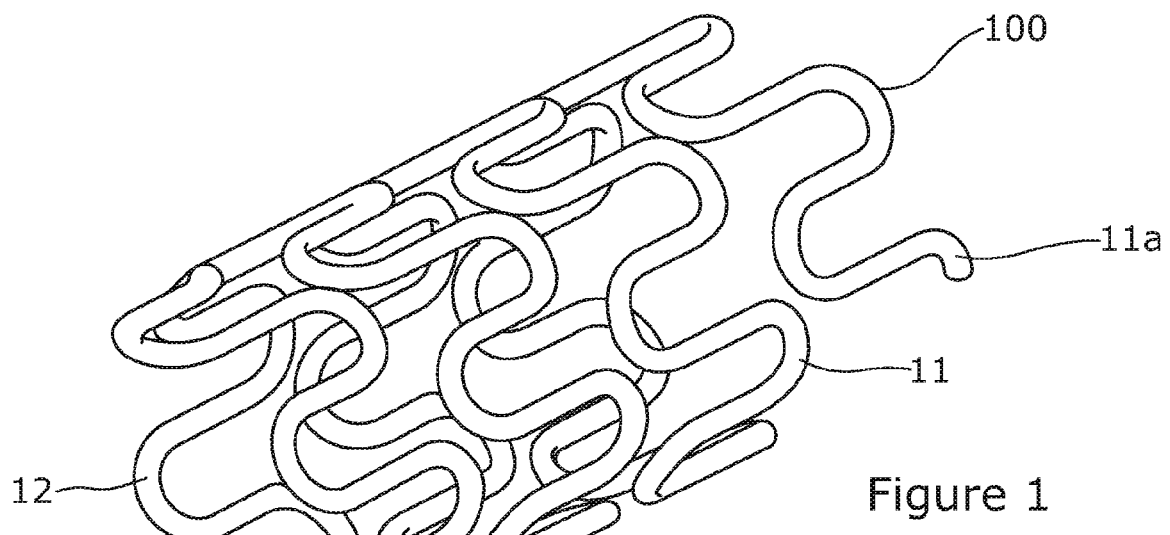
FIG. 1 shows a stent scaffold according to the present invention.

The metal alloy, medical devices and stents of the present invention are now described in further detail.

Alloy

In a first aspect, the present invention provides an alloy which consists essentially of:
3.0 to 5.0% by weight lithium,
0.25 to 4.0% by weight yttrium; and
the balance being magnesium (for example being 91.0 to 96.75%% by weight magnesium) and trace elements.

In one embodiment, the alloy is substantially free of all other rare earth metals beyond trace levels. As used herein the term "trace levels" refers to a content of less than 500 ppm (parts per million), preferably less than 400 ppm, for example less than 300 ppm.

In one embodiment, the alloy has an Fe and Ca content of 150 ppm or lower.

The magnesium is preferably high purity magnesium. The term "high purity magnesium" refers to a magnesium which has greater than 99% purity, for example greater than 99.5% purity, such as 99.8% purity, 99.9% purity or greater than 99.9% purity, such as a purity of 99.99%. Generally a high level of purity is preferred.

Optionally, the present invention provides an alloy which consists essentially of:
3.2 to 4.8% by weight lithium,
0.5 to 2.0% by weight yttrium; and
the balance being magnesium (for example 93.2 to 96.3% by weight magnesium,
preferably is high purity magnesium as defined above) and trace elements.

Optionally, the alloy is substantially free of all other rare earth metals beyond trace levels. The alloy can have an Fe and Ca content of 150 ppm or lower.

Optionally, the present invention provides an alloy which substantially consists of:
3.2 to 4.8% (preferably 3.2 to 4.2%) by weight lithium, 0.5 to 2.0% (preferably 0.5 to 1.5%) by weight yttrium; and
93.2 to 96.3% by weight magnesium, which together with any trace elements sums to 100% of the alloy.

One embodiment is an alloy which consists substantially of 4% by weight lithium, 0.5% by weight yttrium and the balance being magnesium (plus any trace elements).

A further embodiment is an alloy which consists substantially of 4.2% by weight lithium, 0.5% to 1.5% by weight yttrium and the balance being magnesium (plus any trace elements).

The alloy of the present invention has the benefit that the microstructure of the cast ingot is conventional poly-crystalline with predominantly equi-axed crystal dimensions. This is advantageous relative to the columnar or single crystal microstructures of the alloys as described in U.S. Pat. Nos. 8,888,841 and 6,387,332.

The alloy can be melted and formed into an ingot by known processes to maintain lowest level of impurities, then drawn by conventional wire drawing means for magnesium through a series of smaller diameters dies and in-line thermal annealing steps.

Addition of yttrium provides improved yield stress of the Mg—Li system, thereby imparting additional radial strength for the stent to resist compressive forces in vivo In a second aspect, the present invention provides an alloy wire, wherein the alloy has the composition as described above for the first aspect of the present invention. The wire can conveniently be formed from drawing a bar stock and annealing the drawn wire, as is known conventionally.

The alloy can be melted and formed into an ingot by known processes to maintain lowest level of impurities, then drawn by conventional wire drawing means for magnesium through a series of smaller diameters dies and in-line thermal annealing steps. The wire will typically be of circular cross-section, although this is not essential. The appropriate wire diameter or cross-sectional thickness is dependent on the desired end use of the wire.

In one embodiment, wire formed from the Mg—Li—Y alloy of the present invention has a yield stress of 200 MPa or more, for example a yield stress of 250 MPa or more, for example a yield stress of 300 MPa or more. Note that the required yield stress is independent of the wire diameter.

In one embodiment, wire formed from the Mg—Li—Y alloy of the present invention has an elongation of at least 8%, for example an elongation of at least 9%, for example an elongation of at least 10%, for example an elongation of at least 11%, for example an elongation of at least 12%, for example an elongation of at least 13%, for example an elongation of at least 14%, for example an elongation of at least 15%, for example an elongation of at least 16%, for example an elongation of at least 17%, for example an elongation of an least 18%. In some embodiments an elongation of at least 10% is suitable, although increased minimum elongation can be beneficial. In some embodiments a minimum elongation of at least 15% is preferred. Note that the elongation % is by reference to the original length of the wire concerned and is independent of wire diameter.

In one embodiment, wire formed from the Mg—Li—Y alloy of the present invention has a yield stress of 200 MPa or more and an elongation of at least 10%, for example 12%, for example 15% or more.

In one embodiment, wire formed from the Mg—Li—Y alloy of the present invention has a yield stress of 250 MPa or more and an elongation of at least 10%, for example 12%, for example 15% or more.

In one embodiment, wire formed from the Mg—Li—Y alloy of the present invention has a yield stress of 300 MPa or more and an elongation of at least 10%, for example 12%, for example 15% or more.

In one embodiment, wire formed from the Mg—Li—Y alloy of the present invention has a yield stress of 337 MPa or more and an elongation of at least 11% or more.

In one embodiment, wire formed from the Mg—Li—Y alloy of the present invention has a drawn fine poly-crystalline microstructure (not a columnar crystal structure as taught in U.S. Pat. No. 8,986,369). The relatively equi-axed (e.g. poly-hedral or slightly oblong grains) are a result of the starting fine grain polycrystalline structure of the bar stock, wire drawing resulting in some grain orientation in the direction of draw, and then at least one full anneal of the alloy following wire drawing.

Thermal annealing of the drawn wire can be conducted by any conventional means and the procedure can be optimised in the normal way, depending on the exact desired mechanical properties needed. For the wire of the present invention thermal annealing can be carried out at a temperature of from 200 to 350 degrees Celsius for 5-30 minutes. In one example, the wire is annealed at a temperature of approximately 300 degrees Celsius for 20 to 30 minutes Medical Device In a third aspect, the present invention provides an implantable medical device wherein said device comprises an alloy having the composition as described above.

The combination of strength, ductility, ability to plastically deform and bioabsorption would make the alloy of this invention beneficial for a range of medical implants where short term structural support is needed during healing. These include ligating clips for example for reproductive sterilization, suture anchors, bone fixation pins and screws, and internal and skin staples.

Stent Scaffold

In a fourth aspect, the present invention provides a stent scaffold, said scaffold comprising the Mg—Li—Y alloy of the first aspect of the present invention.

Optionally, the stent scaffold comprises the wire of the second aspect of the present invention. Optionally the stent scaffold is substantially formed from the wire of the second aspect of the present invention.

Optionally, the stent scaffold is formed by winding the wire of the second aspect of the present invention around a suitable sized and shaped mandrel to form helical windings. The wire can be annealed on the mandrel so that it maintains its coiled shape once removed from the mandrel. This annealing can be achieved using any suitable method known in the art such as: electrical annealing (where a current is passed through the wire), electromagnetic induction heating, or in a conventional vacuum oven, with or without a supporting mandrel. Depending on the extent of annealing and wire length, the person skilled in the art would be aware that the parameters required above may change. The control parameters used in the electrical annealing are voltage and time. For a given voltage, the resulting current is dependent on length of wire. Therefore, the wire can be annealed for 10 seconds to 30 minutes at 0.1 to 5.0 volts for a given length of wire of between 20 to 100 cm. In one example, once the wire has been formed into a suitable shape, an electrical source is connected at 5 volts for 15 seconds to fully anneal 45 cm of wire. Alternatively the formed scaffold (coiled wire) can be annealed at a temperature of 200 to 350 degrees Celsius for 5 to 30 minutes.

The appropriate wire diameter is dependent on the internal diameter of the vessel to be treated. For coronary size vessels of 2.5 to 4.5 mm diameter, a finished wire diameter of between 60 microns and 150 microns is appropriate. To treat a dissection of a 30 mm aorta, a wire diameter measuring between 0.5 and 2 mm can be used.

Optionally, the wire is formed in two steps. One, the wire is shaped into a repeating waveform, in which the wire adopts a pattern having repeating crowns (peaks) and troughs (see FIGS. 5 and 6). The waveform provides radial strength and stiffness. Two, the repeating waveform is wound helically thereby forming a tubular stent scaffold. The waveform may be annealed, for example by the annealing processes described above, after either of these steps, or after any step in which the wire has been cold worked. Therefore there may be multiple anneals in the manufacturing process of the stent scaffold.

In one aspect, the wire is shaped into a repeating waveform having alternate crowns and troughs connected by longitudinal segments or legs, and the repeating waveform is then helically wound to form a tubular structure. Thus in one aspect, the repeating waveform consists of repeats of a unit waveform, each unit waveform having a first crown segment connected by a first leg to a trough which is connected to a second leg, the second leg being connected to a second crown segment and wherein the second crown segment connects to (and is contiguous with) the first crown segment of the adjacent unit waveform to form a crown.

Optionally, the unit waveform is stepped (see FIG. 4 and FIG. 6) such that an incline is produced. This has the advantage of allowing the helical shape to be more easily formed into the stent scaffold. The stepped waveform is achieved by having one leg or straight longitudinal segment (105) being shorter than the other leg or longitudinal segment (106) of the unit waveform cell.

Thus in one aspect, the stepped repeating waveform consists of repeats of a unit waveform, each unit waveform having a first crown segment connected by a first leg to a trough which is connected to a second leg, the second leg being connected to a second crown segment and wherein the second crown segment connects to the first crown segment of the adjacent unit waveform to form a crown, and wherein the first leg has a different length to the second leg. Optionally the first leg can be longer than the second leg. Alternatively the first leg can be shorter than the second leg.

Figure 9:
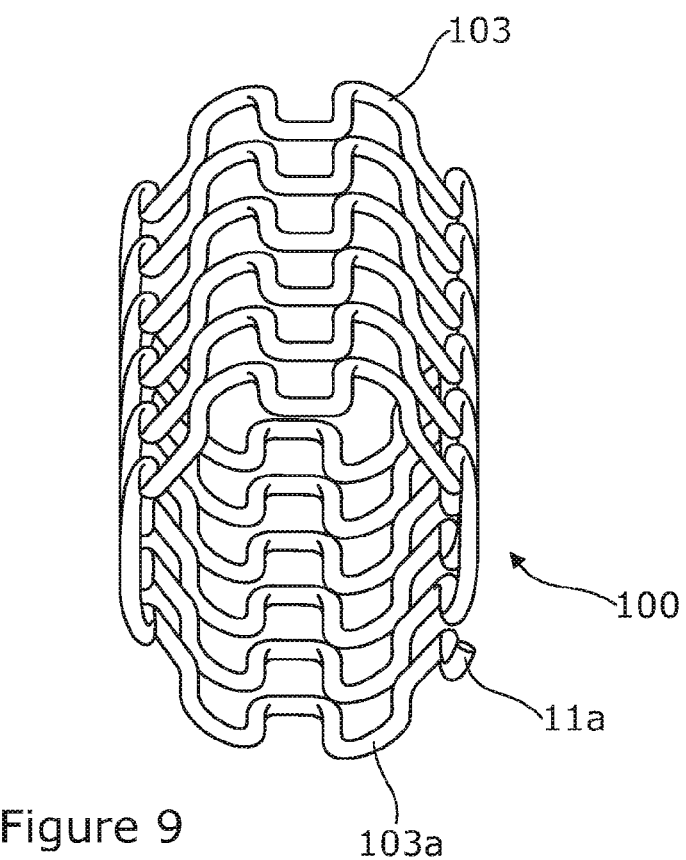
FIG. 9 shows a stent scaffold according to the present invention in which the waveform of FIG. 6 is helically wound so that the peaks and troughs are aligned in the longitudinal axis of the stent scaffold.

In one embodiment, the repeating waveform can be wound helically so that the crowns (peaks) are aligned along the longitudinal axis of the stent scaffold (see FIG. 9).

Figure 10:
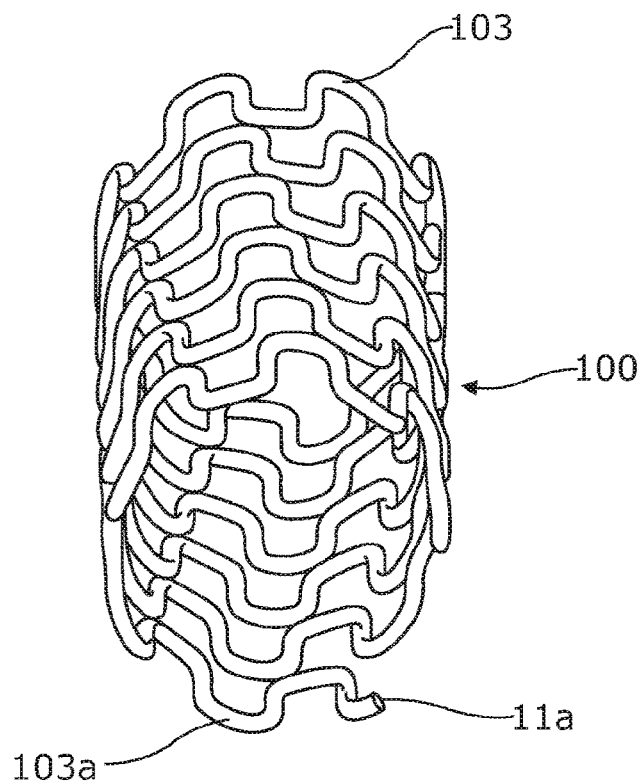
FIG. 10 shows an alternative embodiment of a stent scaffold in which the waveform of FIG. 6 is wound so that the peaks and troughs are aligned to have an anticlockwise orientation.

In one embodiment, the repeating waveform can be wound helically so that the crowns (peaks) are aligned in an anti-clockwise helix relative to the longitudinal axis of the stent scaffold (see FIG. 10)

Figure 11:
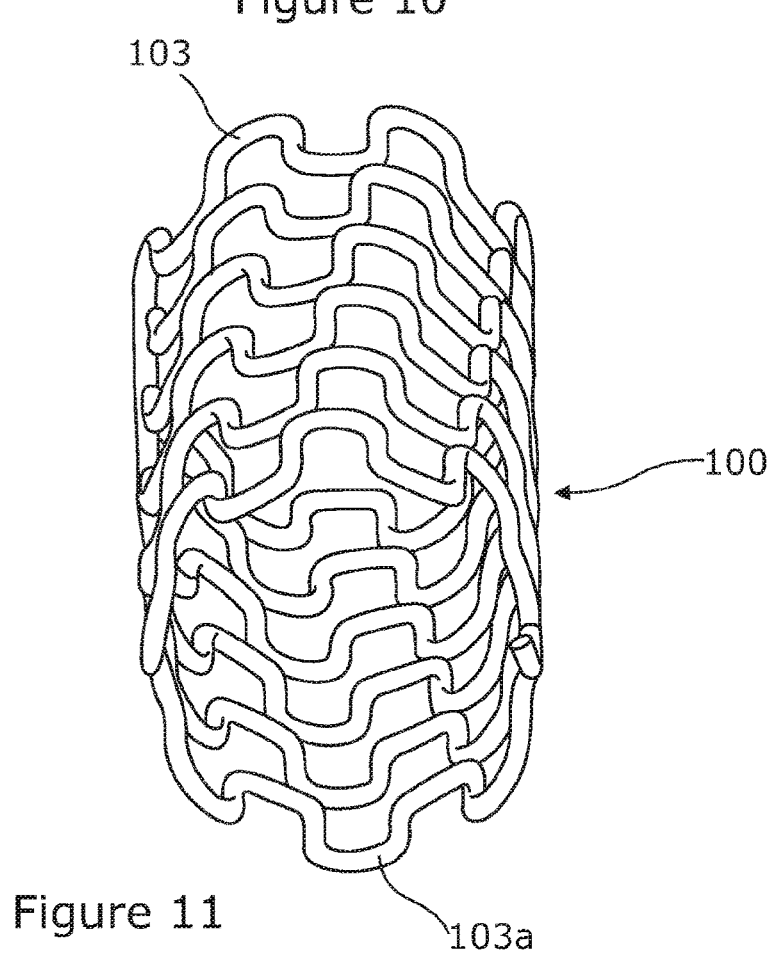
FIG. 11 shows an alternative embodiment of a stent scaffold in which the waveform of FIG. 6 is wound so that the peaks and troughs are aligned to have a clockwise orientation.

In one embodiment, the repeating waveform can be wound helically so that the crowns (peaks) are aligned in a clockwise helix relative to the longitudinal axis of the stent scaffold (see FIG. 11).

The wire of the stent scaffold can itself be wound in either a clockwise or anti-clockwise orientation.

The total height of the waveform in the non-expanded stent scaffold is limited only by the intended end use. Suitable heights of the waveform include from 0.5 to 20 mm. For a scaffold used to treat a dissection of a 30 mm aorta, a total waveform height measuring between 5 mm and 20 mm may be appropriate. For other uses a smaller waveform height may be appropriate, for example 0.5 mm to 1.5 mm. In some embodiments a waveform height of 0.6 mm to 1.4 mm, for example 0.7 mm to 1.3 mm, such as 0.8 mm to 1.2 mm can be used.

In primary embodiments the crowns of the waveform in their formed position (prior to crimping) have an inner diameter, $D_{crown}$ according to the following formula, where the ratio parameter, X is in the range 2.4 to 2.8 and $D_{wire}$ is the cross-section diameter of the Mg—Li–Y wire:

$$D_{crown} = X \times D_{wire}$$

Alternatively, the ratio parameter X can be in the range 2.2 to 3.2.

Figure 3:
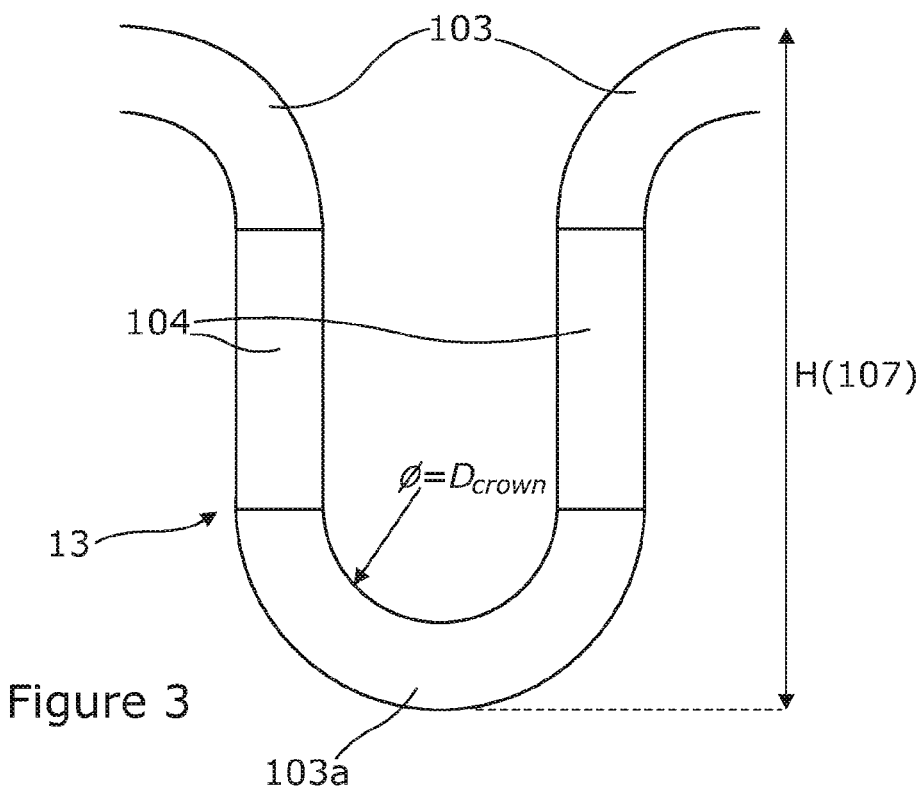
FIG. 3 shows detail of a unit waveform suitable for use in a stent scaffold according to the invention.
Figure 4:
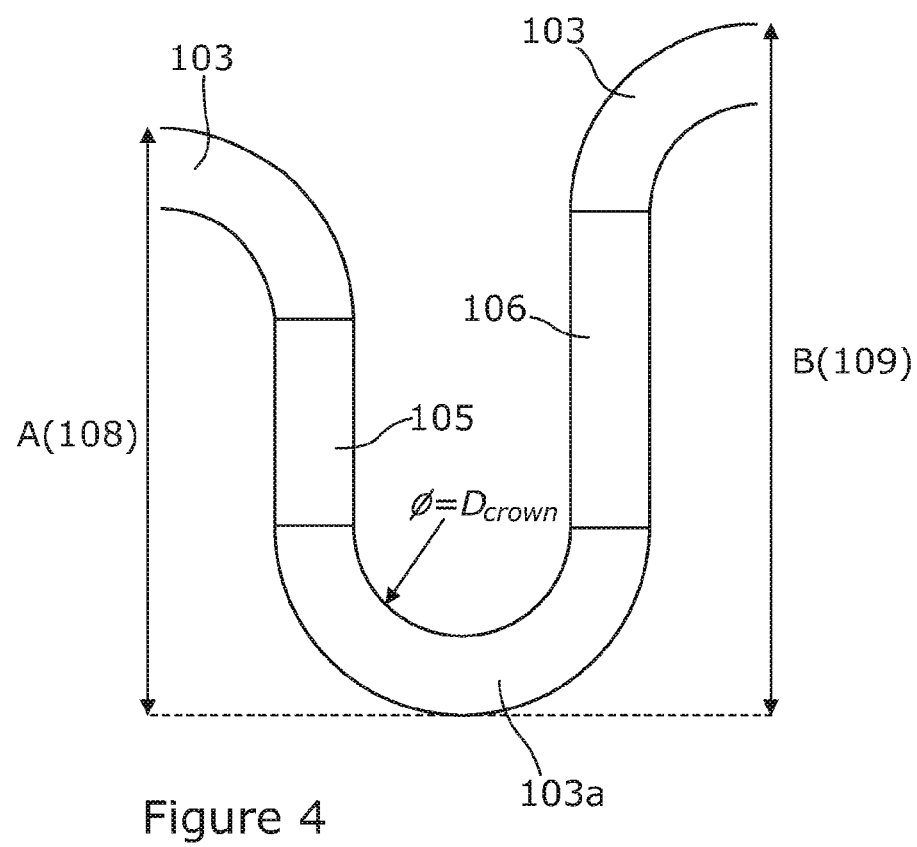
FIG. 4 shows detail of an alternative unit waveform for use in a stent scaffold according to the invention, for example as shown in FIG. 2.

Typically, the number of waves per revolution of the helix will be in the range of 5-8, where a wave is considered a single repeatable unit cell of the waveform (as depicted in FIGS. 3 and 4).

Stent

In a fifth aspect, the present invention provides a stent which comprises a stent scaffold according to the fourth aspect of this invention and further comprises a bioresorbable polymer connector which links at least two turns of the stent scaffold.

Thus the stent according to the present invention can be described as a hybrid bioresorbable vascular stent (BVS). In this context, the term "hybrid" is used to describe a stent structure that includes both metallic and polymeric structural design features, in order to differentiate it from conventional all-polymer or all-metal BVS designs.

The BVS of the present invention is tubular in geometry and expandable from a smaller diameter for insertion in the body on a flexible catheter to a larger diameter appropriately sized for the vessel internal diameter. The expansion can conveniently be achieved by the inflation of a high pressure angioplasty balloon located within the internal lumen of the BVS, when it is mounted upon the distal end of the delivery catheter. The catheter may be inserted into the body lumen through a conventional vascular access device and introducer and guided by fluoroscopy to the site of implantation, where the stent is expanded by means of an inflation port on the proximal side of the catheter. In this context, "distal" refers to the end of the catheter that is inserted in the body lumen first and farthest from (the hands) of the clinician, and "proximal" refers to the end of the catheter that the clinician holds and manipulates during navigating the BVS to the implant site.

As described above, the stent comprises a scaffold formed from a magnesium alloy wire formed into a waveform to provide radial strength and stiffness. The BVS also includes at least one connector, made of bioresorbable polymers to provide additional structural support to the BVS. Optionally, the stent can include two or three connectors. Generally, the connectors connect the waveforms longitudinally.

A function of the longitudinal polymer connectors is to provide structural resistance to longitudinally applied tensile or compressive forces during stent deployment, balloon withdrawal, and in vivo loading. However, a high number or density of longitudinal connectors will render the stent overly stiff and resist bending, which is suboptimal for stent deliverability (threading the mounted stent on a balloon catheter through tortuous vessels to the intended implant site) and for conforming to highly angulated or tortuous vessels after expansion. Also, depending on the width of the connector, the polymer may inhibit the magnesium waveform elements from compressing during crimping or from opening up during balloon expansion. Thus control of connector placement, geometry and width/volume will affect overall stent performance.

The connector can be present along the full length of the stent scaffold, i.e. is a continuous connector and is attached to each turn of the helix of the stent scaffold. Where the polymer connector is a continuous connector generally one, two, three or four connectors will be present. Conveniently the connectors will be spaced equi-distantly around the circumference of the stent scaffold.

Alternatively, the polymer connector can present along only a partial length of the stent scaffold, i.e. is a discontinuous connector. However, each discontinuous polymer connector must still connect between at least two turns of the stent scaffold. For example, the connector is attached to and connects 2, 3, 4 or 5 adjacent helical turns along the length of the stent scaffold. Generally, multiple discontinuous connectors will be present to provide the required degree of connection.

Optionally, a set of multiple discontinuous connectors can be present. Optionally, the longitudinal axis of each connector is aligned with the longitudinal axis of each other connector within the set. Each connector within the set can be in a spaced (preferably equi-distantly spaced) relationship from each other connector of the set. Optionally, the longitudinal axes of the connectors of a set can be aligned with the longitudinal axis of the stent scaffold or can be angularly off-set from the longitudinal axis of the stent scaffold. Optionally two or more (for example three) sets of discontinuous connectors can be present, with each set being spaced equi-distantly around the circumference of the stent scaffold.

In one embodiment, the repeating waveform of the stent scaffold is wound helically so that the waveform crowns are aligned along the longitudinal axis of the stent scaffold and the longitudinal axis of each connector is aligned along the longitudinal axis of the stent.

In one embodiment, the repeating waveform of the stent scaffold is wound helically so that the waveform crowns and troughs are aligned in an anti-clockwise helix relative to the longitudinal axis of the stent scaffold (see FIG. 10) and the polymer connector(s) are follow an anti-clockwise or clockwise spiral.

In one embodiment, the repeating waveform of the stent scaffold is wound helically so that the waveform crowns and troughs are aligned in a clockwise helix relative to the longitudinal axis of the stent scaffold (see FIG. 11) and the polymer connector(s) follow an anti-clockwise or clockwise spiral.

Optionally the connector present at each end of the stent scaffold has an increased mass attached to the last turn of the wire helix. Advantageously, the increased mass covers the free end of the wire. Optionally the free end of the wire is encapsulated within the mass at either or both ends of the polymer connector.

Optionally, the stent comprises at least one connector having an external fin. The fin has an outer facing edge. During deployment, the fin presses against the intima of the vessel wall and causes dissection in a controlled and precise manner.

In a yet further embodiment, the stent according to the present invention comprises two or more stent scaffolds longitudinally connected together by a polymer connector.

As described above, the stent scaffold is formed from a drawn fine wire comprised of 3.2 to 4.8% by weight lithium, 0.5 to 2.0% by weight yttrium, with the balance being high purity magnesium and substantially free of all other rare earth metals beyond trace levels. Optionally, the alloy has an Fe and Ca content below 150 ppm.

To form the wire, the alloy can be melted and formed into an ingot by known processes to maintain lowest level of impurities, then drawn by conventional wire drawing means for magnesium through a series of smaller diameters dies and in-line thermal annealing steps. The appropriate wire diameter is dependent on the diameter of the vessel to be treated. For coronary size vessels of 2.5 to 4.5 mm diameter, a finished wire diameter between of between 60 microns and 150 microns is appropriate. For a scaffold used to treat a dissection of a 30 mm aorta, a wire diameter measuring between 0.5 and 2 mm is appropriate.

Optionally, the alloy comprises 3.2 to 4.8% (by weight) Li, and 0.5 to 2.0% (by weight) Y, and the balance high purity magnesium. In one embodiment, the stent scaffold (100) consists of a continuous waveform wound helically around a mandrel and annealed to form a tubular shape (FIG. 1). In another embodiment, this tubular structure is formed by one continuous 3D process rather than in two steps as described above.

Optionally, the unit waveform is stepped (see FIG. 4 and FIG. 6) such that an incline is produced. This has the advantage of allowing the helical shape to be more easily formed into the stent scaffold. The stepped waveform is achieved by having one leg or straight longitudinal segment (105) being shorter than the other leg (106) of the unit waveform cell.

Figure 7:
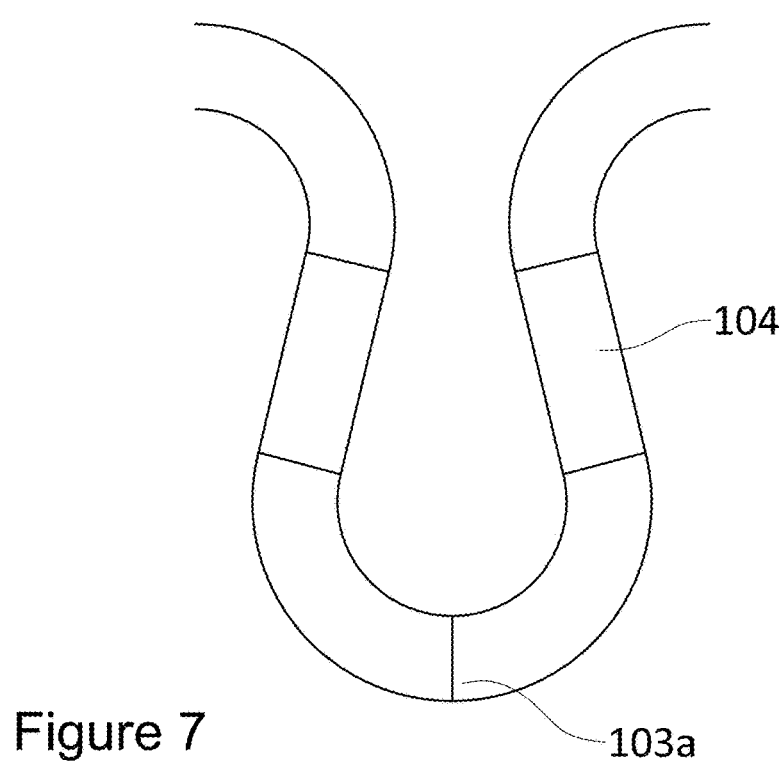
FIG. 7 shows the detail of the unit waveform according to FIG. 3 following compression of the stent scaffold.
Figure 8:
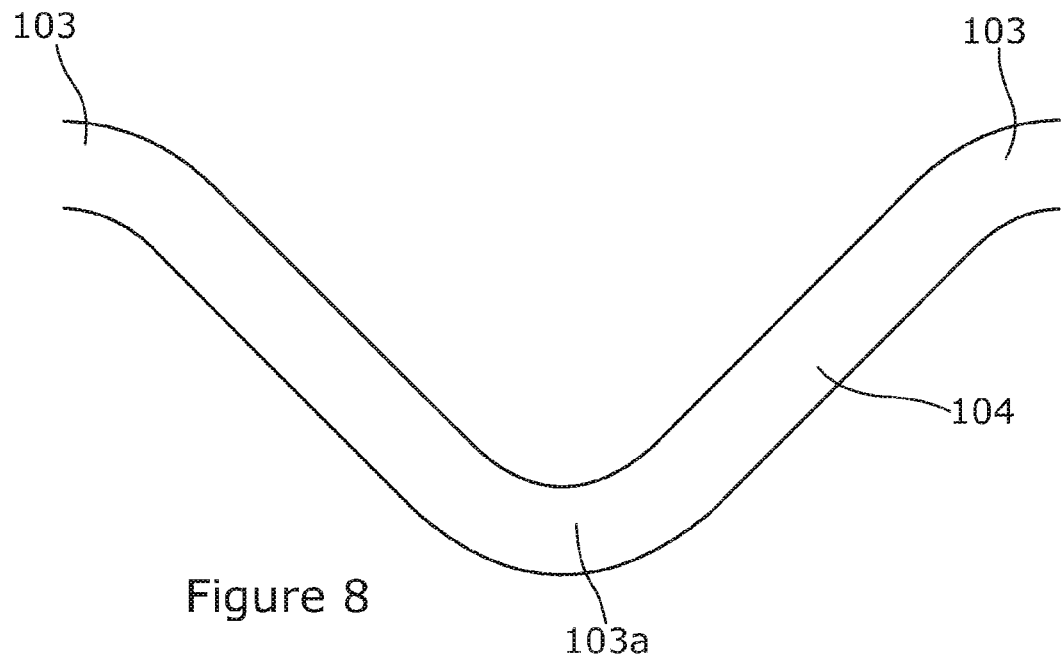
FIG. 8 shows the detail of the unit waveform according to FIG. 3 following expansion of the stent scaffold.

The crown segments of between two adjacent unit waveforms act as hinges during the compression (known as crimping) of the structure onto a balloon catheter and during expansion on implant of device. The strut segments change angle as the waveform compresses or expands, as depicted in FIG. 7 and FIG. 8 respectively. Plastic deformation of the Mg—Li—Y alloy during both crimping and expansion prevents the structure from recoiling to the original formed position.

Figure 2:
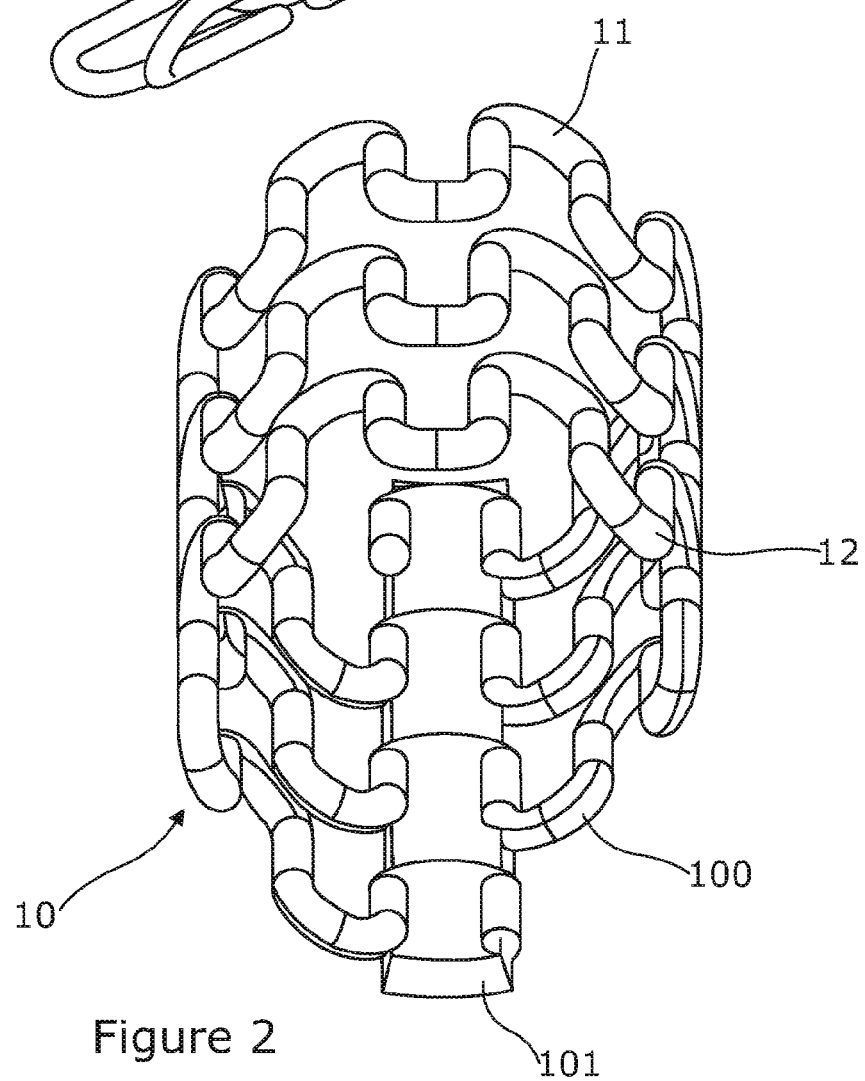
FIG. 2 is a schematic diagram of a stent according to the present invention comprising a stent scaffold plus a polymer connector.

The tubular stent scaffold alone is not a functional stent because it contains no longitudinal connectors necessary for maintaining integrity during expansion and for providing resistance to tensile and compressive longitudinal forces (e.g. column strength). Accordingly, in the present invention connectors (101) of a bioresorbable polymer are provided to bridge adjacent windings of the helix (FIG. 2).

Suitable polymers for the connector include any biocompatible bioresorbable polymers, such as polyesters, for example linear polyesters, in particular aliphatic linear polyesters, for example the poly lactide-glycolide family of homo- and co-polymers and close analogues thereof. Any suitable molecular weight which provides the desired absorption time can be used. A suitable absorption time is 6 months to 2 years, for example 9 months to 18 months, for example 9 months to 15 months, such as approximately one year. Mention can be made of polymers having a molecular weight of 50 k to 100 k g/mol as being suitable.

As described above, the BVS comprises at least one connector that is formed from a bioresorbable polymer. The polymer can be from the family of lactide-glycolide copolymers and or homopolymers or analogues thereof. These polymers are typically linear aliphatic polyesters that show full absorption (90% mass loss at the implant site) by one year post-implant. Suitable polymers include amorphous copolymers of 20-30% by weight glycolide and 70-80% by weight lactide, the polymer having a molecular weight greater than 70 k g/mol. In another example, the connector can be formed of PLGA having more than 90% by weight glycolide and the remaining content being lactide with a starting molecular weight greater than 80 k g/mol, which demonstrates full absorption in 9 months. Alternatively, the polymer can be a semi-crystalline PLGA of greater than 90% by weight with up to 10% by weight glycolide, with a starting molecular weight of approximately 60 k g/mol. Other embodiments of polymer connector materials include polycaprolactone-lactide (PCL-PLA) copolymers and polydiaxanone (PDS or PDO) with molecular weights of 50 k to 100 k g/mol.

The bioresorbable polymer connectors can be formed by a variety of means. In one embodiment, the connectors can be pre-extruded filaments that are arranged on the surface of the stent scaffold, and then melted into the plane of the wire waveform by the action of heat and pressure, for example when heated and compressed in a two-part mold with an inner core or mandrel. The resulting structure is a functional stent capable of balloon expansion with adequate column strength and axial flexibility.

Another embodiment uses a different and novel method of forming the polymer connectors, which is to melt extrude them onto the surface of the stent scaffold. A modified '3D Printer' of the type used for Fused Deposition Modelling or FDM can be used. This manufacturing method offers a variety of advantages in design, speed and accuracy of manufacturing, and functional performance. Several design variants including helical connector patterns, non-continuous connectors have been demonstrated which offer benefits to stent flexibility and crimpability, and to achieve a stent capable of inducing spiral blood flow in vivo.

Optionally, to consolidate the connection of the 3D printed polymer, shrink wrap can be used after printing to compress the polymer connectors into the wire at a pre-defined diameter.

In more detail, a commercial 3D printer ("3DP") (for example Hephestos 2, from company BQ) is modified so that it 'prints' on to a numerically controlled rotating mandrel at a fixed height (rather than the conventional printing on to a x-y space with cumulative z-direction layers). In the modified 3D printing process of this invention, the printer head is driven predominantly in only one direction (Z) while the mandrel is driven in angular rotation through an algorithm programmed into the machine's G-code. A starting filament of polymer (for example 1.75 mm PLLA) is melted and precisely extruded onto the rotating surface of the stent scaffold through a nozzle. The nozzle size can be selected to provide the desired thickness to the connector, for example the nozzle can have an internal size of 0.5 mm or less, for example 0.2 mm. To improve the adhesion of connector to the stent scaffold, the wire of the stent scaffold can optionally be heated during printing to a temperature of between 40-60° C. We have found that adequate adhesion is achieved by directly melt extruding the bioresorbable polymer on to the heated wire of the stent scaffold.

Importantly, the scaffold structure formed by the melted bioresorbable polymer connectors partially envelop the struts of the stent scaffold, resulting in a mechanical bond that can be preferentially decoupled during expansion in very tortuous or angulated anatomy, e.g. blood vessel. Thus in one embodiment, the stent of the present invention comprises at least one connector which is bonded to the stent scaffold so that if it is positioned at a location within the lumen of a body vessel which is highly angulated during expansion of the stent, the connector at least partially uncouples from the stent scaffold during expansion. This ability for preferential decoupling is a distinct advantage over all magnesium laser cut hypo-tube designs where the multi-dimensional stress condition at the juncture point of rings and longitudinal connectors can lead to early catastrophic ring fracture and loss of wall apposition of the struts. Magnesium alloys are typically highly vulnerable to this failure mode due to its brittle nature under multi-directional loading due to its limited crystallographic slip planes, whereas the hybrid stent design of this disclosure mitigates this weakness. The preferential decoupling is possible due to the reduced cross-sectional area of the connector at the point(s) where it cross the wire of the stent scaffold. The reduced cross-sectional area means that any break will occur at that location, i.e. at a controlled and pre-determined point. Allowing a controlled release of the stent scaffold from at least one connector allows the stent to adapt to the curvature of a highly tortuous body lumen (e.g. blood vessel) without loss of apposition between the stent and the lumen into which it is being deployed.

The advantage of the 3D printing manufacturing method for the formation of the polymer connectors is that it enables a variety of design options that translate to improved stent properties such as longitudinal flexibility, ability to crimp, better adhesion and end fixation, and helical patterns that promote a more physiologic flow in vivo.

In one embodiment, the 3DP is programmed to print additional polymer volume (1.25× to 2.0×) at the end fixation point relative to the normal longitudinal connector volume to insure end fixation without making the entire stent overly rigid.

Thus, the present invention further provides a method of producing a hybrid stent, wherein said process comprises: using a 3D printer to extrude a polymer onto the surface of a stent scaffold to form a polymer connector thereon.

Optionally, the stent scaffold is heated during the printing process, for example is heated to the transition temperature of the polymer, for example is heated to a temperature of between 40 to 60° C.

Optionally the stent scaffold is mounted onto a rotating mandrel which is linked to the 3D Printer.

Optionally, only a single layer of polymer is deposited onto the stent scaffold during printing.

Optionally, to consolidate the connection of the 3D printed polymer, shrink wrap can be used after printing to compress the polymer connectors into the wire at a pre-defined diameter.

It can be advantageous to coat the ends of the stent scaffold with a primer coat of bioresorbable polymer prior to fixation of the polymer connector(s). The primer coat can be formed using a dilute solution (for example 10% polymer solids in a suitable solvent, such as ethyl acetate or THF) of a suitable bioresorbable polymer. Suitable bioresorbable polymers for use in the primer coat include polyesters, such as aliphatic polyesters. Homo- or co-polymers of PGLA can be used. The bioresorbable polymer used in the primer cost can be the same or different to the bioresorbable polymer used for the connector(s). The primer coat can typically have a thickness of 20 microns or less, for example 10 microns or less. The primer coat can be applied to one or both ends of the stent scaffold or can be applied to substantially all of the stent scaffold, for example all of the stent scaffold. The primer coat can be a conformal layer with a thickness of 20 microns or less, for example 10 microns or less. The primer coat can be achieved by any conventional technique, for example spray coating, vapour deposition, dip coating or the like. Inclusion of a polymer primer coat provides higher polymer to metal adhesion, which can be particularly advantageous at the ends of the stent. Thus, including a polymer primer coat has the advantage that stent unravelling during expansion can be prevented. The present invention further provides a catheter loaded with a stent according to the present invention. Generally, the catheter will include an expandable balloon located within the lumen of the stent which will be inflated (once the stent has been positioned at the desired location) to cause expansion thereof.

The present invention provides a method of treatment of a body lumen, said method comprising:
 a) inserting a catheter loaded with a stent according to the present invention into said body lumen; and
 b) causing expansion of said stent at the desired location of said lumen.

Preferred or alternative features of each aspect or embodiment of the invention apply mutatis mutandis to each aspect or embodiment of the invention (unless the context demands otherwise).

The term "comprising" as used herein means consisting of, consisting essentially of, or including and each use of the word "comprising" or "comprises" can be independently revised by replacement with the term "includes", "consists essentially of" or "consists of".

These and other objects of the invention are provided by one or more of the embodiments described below.

DETAILED DESCRIPTION OF THE DRAWINGS

As shown in FIG. 1, the stent scaffold (100) is formed from a continuous wire (11) shaped into a continuous waveform (12). The waveform (12) describes a pattern of alternating crowns (peaks) and troughs (shown in more detail in FIGS. 3 and 4). Waveform (12) is wound into a helical shape of at least 3 revolutions to form a tubular shape, preferably a cylindrical shape of constant diameter.

In FIG. 1, the crowns and troughs of waveform (12) are aligned in the direction of the longitudinal axis of stent scaffold (100), i.e. each complete circumference ("turn") of the stent scaffold is formed from a whole number of waveform units. In an alternative embodiment, the crowns and troughs need not be aligned in this manner, but can be slightly off-set from each other in adjacent turns of the stent scaffold (100).

Whereas U.S. Pat. No. 8,888,841 teaches rings connected by polymer connectors, the continuous waveform used in the stent scaffold (100) offers ease of manufacturing in terms of controlling spacing of windings and continuous manufacture. The helical form also provides structural advantages, such as improved resistance to torque, and general structural stability against axial shear forces.

FIG. 2 shows a stent (10) according to the present invention. The stent (10) as illustrated comprises a stent scaffold (100) (for example as illustrated in FIG. 1) and a connector (101) formed from a bioresorbable polymer. As illustrated, stent scaffold (100) is formed from 3 helical turns of waveform (11) but could likewise be formed from more (or fewer) helical turns to provide a stent (10) of the required length. The polymer connector (101) consists of a continuous polymer strip which runs the whole length of stent scaffold (100). Polymer connector (101) can be formed from any suitable biocompatible and bioresorbable polymer, for example can be formed from a polylactide such as PLGA. Optionally polymer connector (101) can be formed by 3-D printing onto the surface of stent scaffold (100). Polymer connector (101) runs from the lower end (as illustrated) of the stent scaffold (100), covering the free end (11*a*—see FIG. 1) of wire (11) along the whole length of stent scaffold (100) to the upper end (as illustrated), again covering the free end of wire (11*a*). This arrangement ensures that neither free end (11*a*) of wire (11) can snag during release of stent (100) from the catheter or otherwise during deployment of the stent (100).

FIG. 3 shows the detail of a waveform unit cell (13) which repeats to form waveform (12) of stent scaffold (100). The waveform (12) is formed from a wire (11) of a Mg—Li—Y alloy according to the invention. The waveform unit cell (13) comprises a series of curved crown segments (103), curved trough segments (103*a*) and joining straight longitudinal strut segments (104), all of circular cross-section. The internal diameter of the curved trough segment (103*a*) is identical to the internal diameter of the curved crown segment (103) and is defined as $D_{crown}$. The height of the waveform unit cell (13) is shown as the arrow labelled H (107). A continuous strip consisting of repeating waveform unit cells (13) of FIG. 3 forms the waveform (12) shown in FIG. 5.

FIG. 4 shows detail of an alternative embodiment of a waveform unit cell (13) which repeats to form waveform (12) of stent scaffold (100). The waveform (12) is formed from a wire (11) of a Mg—Li—Y alloy according to the invention. As for FIG. 3, the waveform unit cell (13) comprises a series of curved crown segments (103) curved trough segments (103*a*) and joining straight longitudinal strut segments (105, 106). The internal diameter of the curved trough segment (103*a*) is identical to the internal diameter of the curved crown segment (103) and is defined as $D_{crown}$. The height of the strut at each side of waveform unit cell (13) is shown by the arrow labelled A (108) and by the arrow labelled B (107). The waveform unit cell (13) of FIG. 4 is "stepped", that is the length of strut (105) is different to the length of strut (106). Accordingly, the height of the unit cell (13) is different on each side; compare height of arrow A (108) which is smaller than the height of arrow B (109). The reverse configuration is also possible, i.e. to have the height A of strut (105) greater than the height B of strut (106).

Referring to FIG. 3, in the embodiment shown the total height, H (107) of the waveform is typically in the range 0.8 to 1.2 mm. In the case of a stepped waveform as shown in FIG. 4 the effective total height, H is considered the average of lengths A (108) and B (109) depicted in FIG. 4. A suitable waveform height is again typically in the range 0.8 to 1.2 mm.

The waveforms (13) shown in FIGS. 3 and 4 can be helically wound, for example around a mandrel to form a stent scaffold (100). The stent scaffold (100) will generally comprise at least three complete turns. Generally, the helically wound waveform (12) is annealed whilst on the mandrel. Annealing can be achieved through controlled heating. This is attained through electrical annealing where a current is passed through the wire, heating it to the desired temperature on the mandrel, ensuring the tubular shape formed is maintained once removed. Alternatively, the helically wound wire can be placed into an oven and heated prior to its removal from the mandrel.

Figure 5:
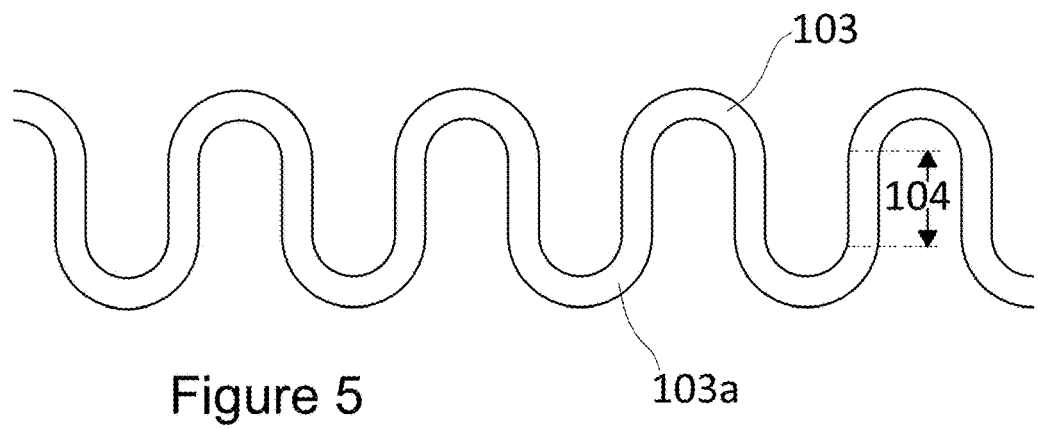
FIG. 5 shows an extended waveform for use in a stent scaffold according to the invention.
Figure 6:
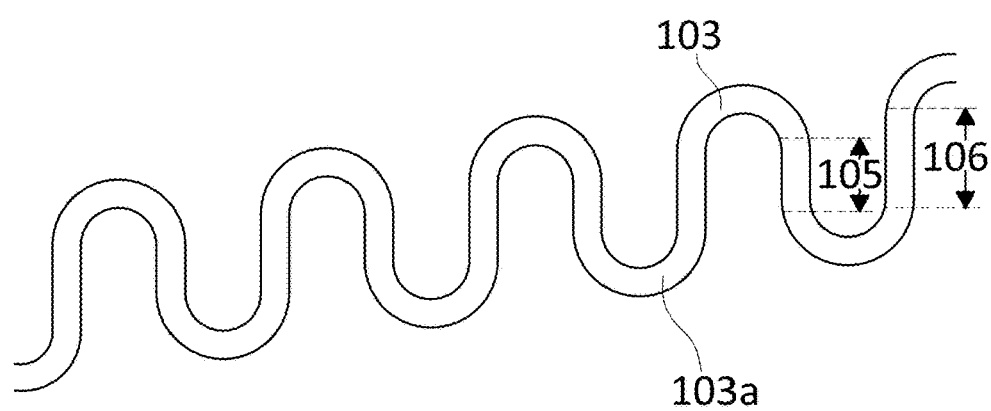
FIG. 6 shows an alternative embodiment of an extended waveform for use in the stent scaffold according to the invention, for example as shown in FIG. 2.

FIG. 5 and FIG. 6 show the waveform (12) produced by repeating the waveform unit cell (13) of FIG. 3 and FIG. 4, respectively. One embodiment consists of Mg-4.0Li—0.5Y alloy with a wire diameter of 125 µm, an X value of 2.52, and a total wave height of 0.95 mm. The X value refers to the ratio of $D_{crown}$ to $D_{wire}$. An advantageous combination of properties including initial radial strength of at least 4.0 N/mm, a strength retention rate to maintain integrity through healing, and then full absorption at the implant site in approximately one year is obtained.

As the waveform (12) of the stent scaffold (100) compresses or expands, the strut segments change angle as depicted in FIG. 7 and FIG. 8 respectively. Thus FIG. 7 illustrates the change of the unit cell of FIG. 3, with the struts (104) of the unit cell (13) pushed together during compression of the scaffold (100). Compression typically occurs during loading of the stent (10) onto the delivery catheter prior to delivery in a process termed "crimping". FIG. 8 shows the change of the unit cell of FIG. 3, with the struts (104) of the unit cell pulled apart during expansion of the scaffold (100) as the stent (10) is deployed. A similar change in strut angle during compression and expansion would also occur for a stent formed using the unit cell shown in FIG. 4.

The stent scaffold (100) formed from wound wire (11) in a waveform structure (12) can have different crown (103) alignments, depending on number of waveforms (12) per revolution of the stent scaffold (100) and the spacing between adjacent turns of the helix. FIGS. 9, 10 and 11 depict three different exemplary arrangements. FIG. 9 shows crowns (103) on adjacent helical turns or layers following a straight path parallel to the central longitudinal axis of the stent scaffold. In contrast, FIGS. 10 and 11 each show an arrangement where the crowns (103) on adjacent helical turns follow a curved path, or more accurately their own helical path, around the stent scaffold (100). In these embodiments, the change in crown (103) alignment affects the ability to accurately apply connecting polymer to the structure and allows for a higher density waveform pattern to be used per unit stent length by optimising these variables. This increase in material within the stent will have a direct effect on the radial strength and absorption time of the stent.

Figure 12A:
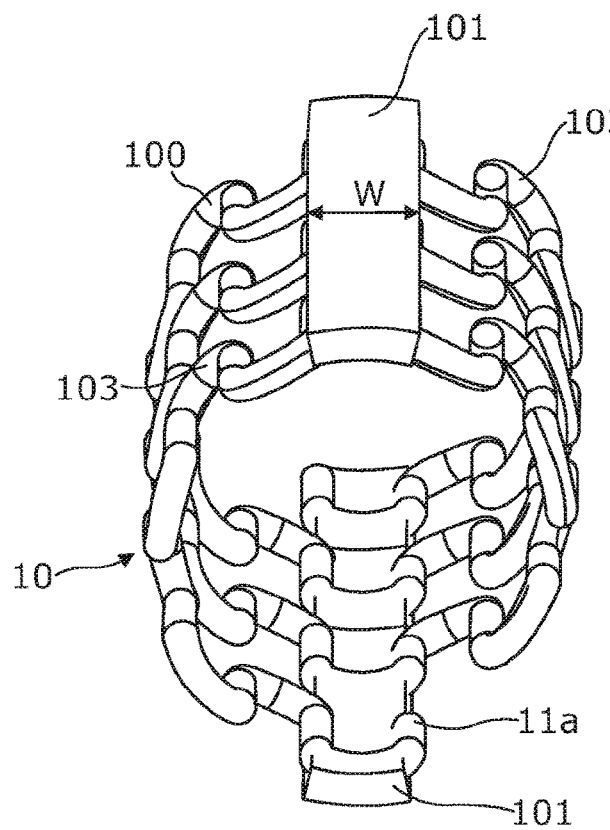
FIG. 12A is a schematic diagram showing an embodiment of a stent according to the invention which has 2 connectors along the length of the stent scaffold.

FIG. 12A shows a stent (10) according to one embodiment of the present invention. As shown, stent (10) consists of a stent scaffold (100) formed by multiple turns of a wire (11) in a waveform pattern. As illustrated, the crowns (103) of the waveform (12) are aligned in the axial direction of stent (10). The embodiment illustrated in FIG. 12A shows two polymer connectors (101). The polymer connectors (101) are positioned diametrically opposite each other on the circumference of stent (10). Alternatively, the width (W) of the polymer connector (101) can be defined as being from a value equal to the diameter of wire (11) and up to a value equal to 5 times the diameter of wire (11). The "width" of the polymer connector as discussed here refers to the dimension of the connector which is orientated around the circumference of the stent scaffold as is illustrated as W in FIG. 12A. The embodiment illustrated shows both polymer connectors (101) running the whole length of the stent (10). Note that, for convenience, the stent (10) is shown consisting of only 3 helical turns of wire (11), but may consist of more helical turns, to provide the desired length of stent (10). The free ends (11a) of wire (11) can conveniently be covered by or embedded within the polymer connectors (101). Any method of forming the polymer connectors (101) can be used, but conveniently the connectors (101) are formed by a process of 3-D printing, for example using a 0.2 mm nozzle and optionally preheating the wire (11) of the stent scaffold (100).

Figure 12B:
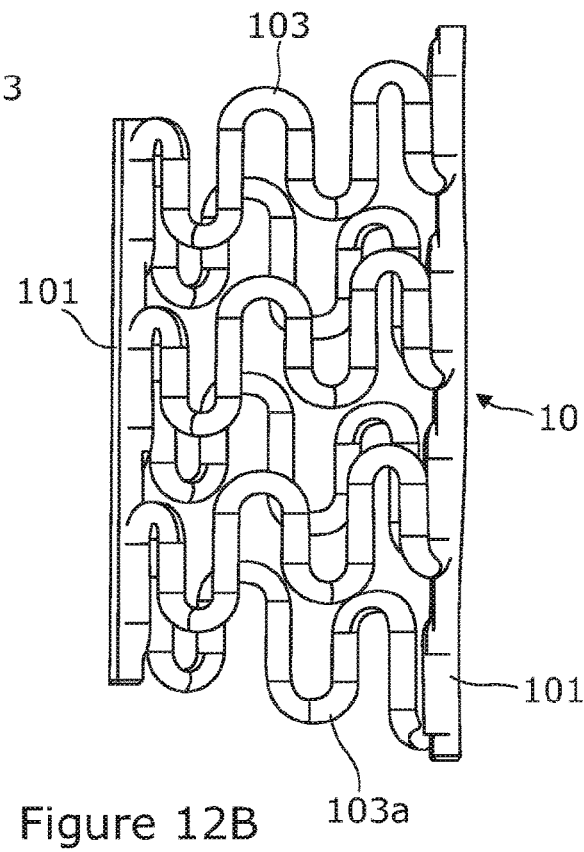
FIG. 12B shows the embodiment of FIG. 12A when viewed from the side.

FIG. 12B shows the embodiment illustrated in FIG. 12A when viewed from the side. Note that the connectors (101) need not be of equal length. In the embodiment shown, the waveform (12) has a stepped waveform unit cell (13) (see FIG. 4) which assists in producing the helical arrangements of the waveform (12).

Figure 13A:
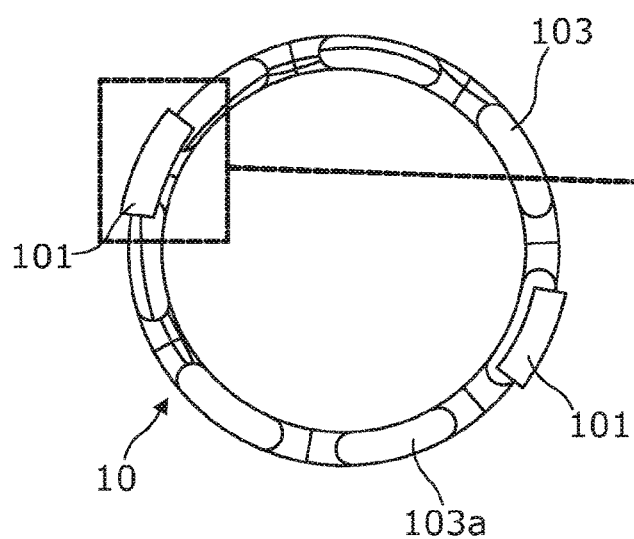
FIG. 13A shows the embodiment of FIG. 12A when viewed from the top.
Figure 13B:
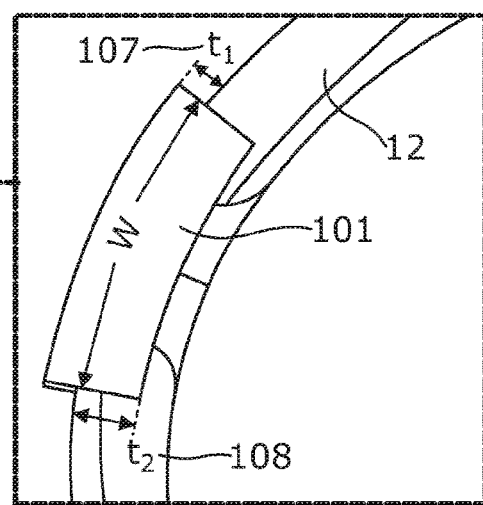
FIG. 13B shows detail of the connector in the boxed section of FIG. 13A.

FIG. 13A shows the embodiment illustrated in FIG. 12A when viewed from the top. The diametrically opposed positioning of each polymer connector (101) around the circumference of the stent scaffold (100) is clearly shown. The boxed section of FIG. 13A is shown in expanded view in FIG. 13B. Polymer connector (101) is located on the outer surface of the stent scaffold (100), and is positioned substantially around the thickness of wire (11) which forms waveform (12).

As shown, a first portion of the polymer connector (101) having a thickness $t_1$ (107) extends outwardly from the surface of the waveform (12). Thickness $t_1$ is typically equivalent to 20 to 50% of the wire diameter used within the stent scaffold. A second portion of the polymer connector extends inwards, overlapping the wire of the stent scaffold in the radial direction by a thickness $t_2$ (108) between 50-100% of the wire diameter (FIG. 15). The width (W) of the or each polymer connectors (101) (as defined above) generally ranges from 100% to 500% of the wire diameter, except at the stent ends where increased width of connector can optionally be used for improved end fixation. If the polymer connector (101) has a width which exceeds this limit, then the connector (101) may negatively inhibit the subsequent crimping and expansion of the stent at that location. Having the width (W) of the polymer connector equal to 100% to 500% of the wire diameter ensures that the connector is bonded to the stent scaffold such that if this portion of the connector is positioned at a location within a highly angulated lumen of a body vessel during expansion of the stent, the connector will at least partially uncouple from the stent scaffold during expansion. In some embodiments, the width of the connector can be determined so that the connector will preferentially break away from the wire of the stent scaffold during deployment of the stent in such a highly tortuous lumen. Further, the width of the connector can be determined so that the connector will preferentially break away from the wire and the connector will break into two pieces during deployment of the stent in a highly tortuous lumen.

Figure 14:
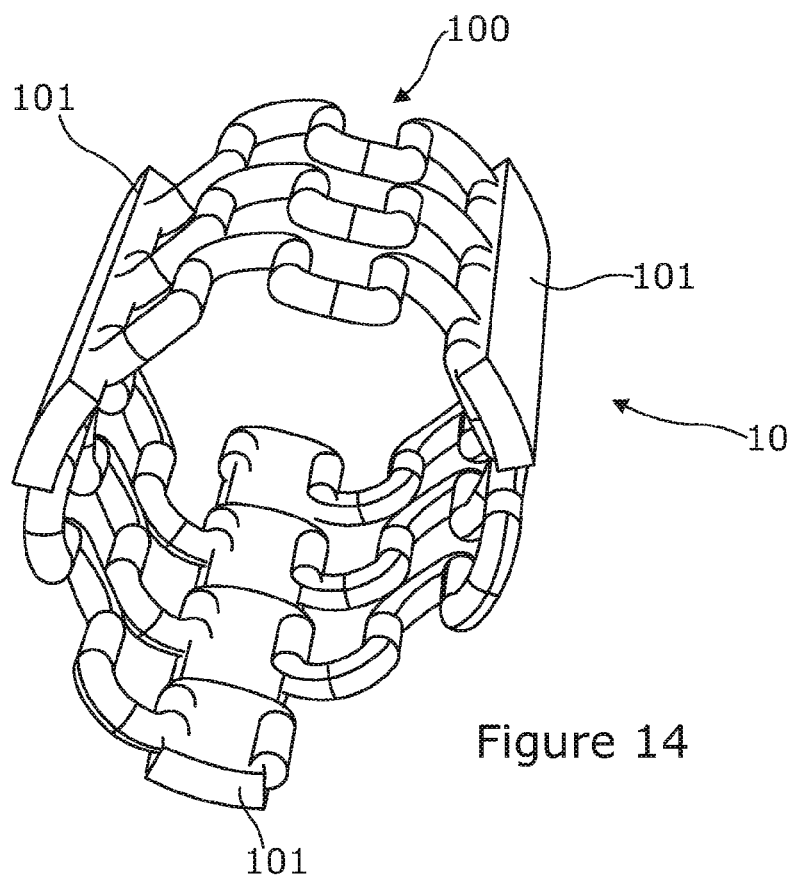
FIG. 14 is a schematic diagram showing an embodiment of a stent according to the invention which has 3 connectors along the length of the stent scaffold.

In the simplest embodiment, a single longitudinal continuous connector (101) of generally constant width (W) is formed with no angular rotation along the full length of the scaffold (100) (FIG. 2). In another embodiment, a second similar continuous connector (101) is formed at 180 degrees spacing to the first (FIGS. 12A, 12B and 13A). In yet another example, three continuous connectors (101) each with no angular rotation are spaced at approximately 120 degrees spacing around the stent scaffold (100) (FIG. 14).

Figures 15A, 15B:
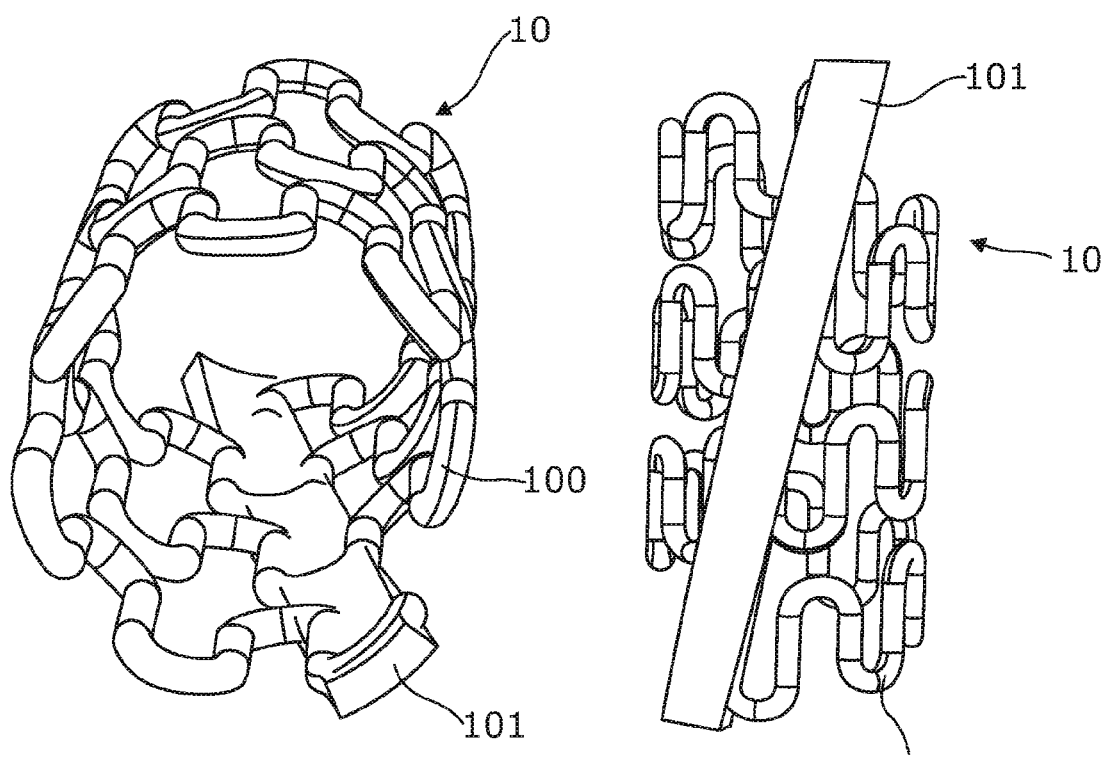
FIG. 15A shows a further embodiment of a stent according to the present invention in which the connector is orientated to have a helical direction.
FIG. 15B shows the embodiment of FIG. 15A when viewed from the side.
Figure 20:
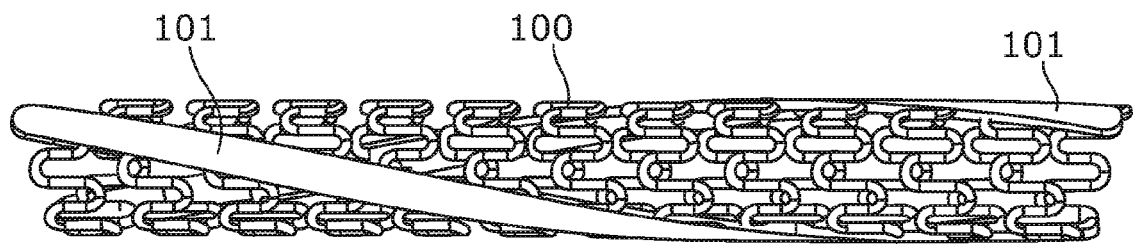
FIG. 20 shows a stent according to the present invention having two continuous connectors, each with helical orientation.

In another embodiment, a single continuous polymer longitudinal connector (101) is formed such that it follows a helical path along the length of the stent (FIGS. 15A and 15B). In one such example, the connector (101) travels through 180 degrees of rotation over approximately 40 mm of the length of the stent, although other pitch angles could alternatively be used, for example from 120 degrees to 240 degrees, and the invention is not limited to any particular pitch angle. Similar to the embodiments described above for the connectors lacking any angular rotation, double or triple helical, continuous connectors of the same pitch and direction can be added spaced around the circumference of the stent scaffold (100) at 180 and 120 degrees respectively. All helical connectors on a single BVS follow the same direction around the structure, preventing any cross linking of polymer connectors.

In one embodiment, the waveform (12) is wound in a helical trajectory to form a tubular stent scaffold (100) prior to printing of the polymer connector (101). The waveform (12) can be wound in a 'right hand' helix, and then the polymer connector (101) can be printed in a 'left hand' helix (or multiple helices) resulting in a balanced structure able to resist applied torque. (FIGS. 16A and 16B).

In an alternative embodiment, both the stent scaffold (100) and the connectors (101) follow the same direction of travel (i.e. both scaffold and connectors are 'left handed' helices or both scaffold and connectors are 'right handed' helices), which affords a structure with less resistance to expansion and more capable of creating localized helical blood flow which is believed to have physiologic benefits.

In another embodiment, the continuous longitudinal connectors (101) include an end section (110) with a width or volume increased by at least 30% to improve the mechanical strength of the terminal connection at the free ends of the wire forming the stent scaffold (100) as shown in FIG. 17.

Whereas the examples described above use continuous polymer longitudinal connectors (101) of constant width and volume which provide the highest level of structural integrity, the trade-off is reduced axial flexibility of the stent which is essential for deliverability and to accommodate highly angulated vessels.

In another embodiment, the stent (10) includes at least one polymer connector (101) that is non-continuous (or discontinuous). Thus, two or more non-continuous longitudinal connectors (101) spaced apart from each other by a section (111) of at least 1 mm in length can be provided. FIG. 18 shows a stent (10) which includes three discontinuous polymer connectors (101a, 101b, 101c) having a gap (111) greater than 1 mm with between each neighbouring pair of connectors. Thus, a complete break in continuity (111) between two connectors (101) is present. In one embodiment, the interrupted design is formed by controlling the 3D printing filament advancement or dwell through the modified software to shut off the extrusion while the nozzle moves relative to the stent (10). In another embodiment, a continuous connector (101) is printed and then subsequently sections of the polymer connector (101) are removed by laser cutting/ablation with an appropriate energy source tuned to the polymer and not the magnesium alloy of wire (11).

In one example, the 125 micron diameter round wire of Mg-4.2Li-1.5Y alloy is formed into a stepped waveform that is then helically wound on a 1.6 mm mandrel and annealed. The tubular stent scaffold (100) is then 3D printed with two helical interrupted polymer connectors (101) that are off-set by 180 degrees. For every connector (101) positioned at the stent end at least 3 helical windings of the wire waveform (12) are encompassed to ensure end fixation. The breaks are 2 mm in length and are staggered so that there is always at least one solid connector at any cross-section along the stent length (FIG. 19).

In another embodiment, the positions of connectors (101) are aligned relative to the wire helix. In all cases, centerlines of the connectors (101) follow the crowns (103) in adjacent layers/turns of the helix through the stent (10). In one embodiment the path of the connectors (101) is defined by following the closest crown (103) in the adjacent layer. FIG. 12A through 20 demonstrate this.

The importance of spiral flow of blood in normal arterial physiology has been recognized to reduce shear stress on the vessel wall and endothelium. Previous attempts to impart spiral flow in stented vessels or in vascular grafts have shown apparent reduced restenosis rates. Technological approaches to imparting spiral flow to date have included heat setting self-expanding stents into a 3D helix that reshapes the vessel accordingly. Another approach is to mold an internal helical fin within a PTFE graft that channels the blood into helical flow.

In the present invention, the stents with helical connectors (101) are also capable of inducing helical flow in a blood vessel. In particular, differential embedding of the wire (11) forming the stent (10) is caused at the location of the connectors (101) which resist embedding into the vessel intima, creating an internal helical protrusion. For example, in FIG. 21 helical channel (200) is formed by differential embedding of the wire (11) at the locations (201) of the polymer connectors (101), in contrast to the location (202) of the wire forming the stent scaffold (100) which is not embedded within a polymer connector (101) and which results in optimal intima wall embedding at such locations (202). Following balloon expansion, internal helical channels which follow paths between the protrusions (101) are thereby created and this helical path induces spiral flow along the length of stent (10). This is achieved by the relatively wide polymer connector (101) (having a width W of up to 500% of the wire diameter), which is unable to fully embed in the vessel wall during high pressure balloon deployment in contrast to the thin wire struts that comprise the majority of the stent (10). This effect is strongest for one or two continuous helical connector designs (FIG. 20), but is anticipated to be present for all the continuous and interrupted connector designs described herein.

Figure 21:
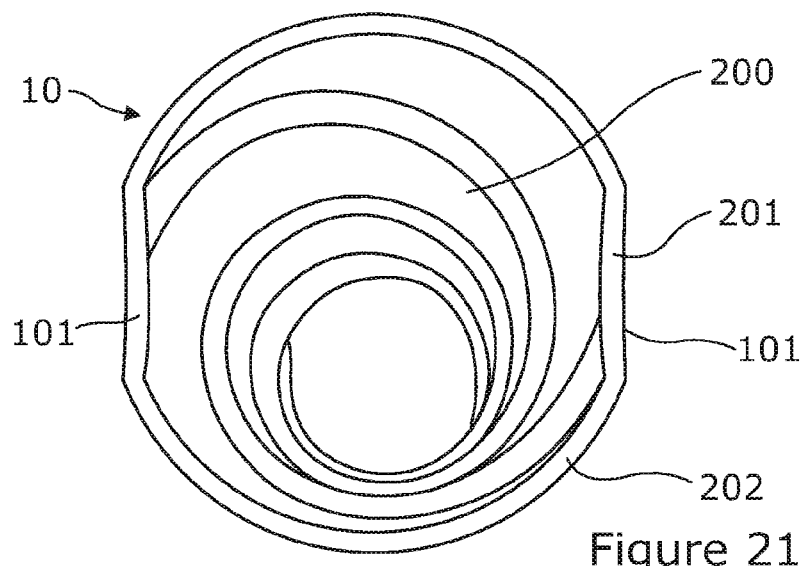
FIG. 21 is a schematic diagram showing how reduced embedding at the location of polymer connectors causes internal helical protrusions within the lumen of the stent.

FIG. 21 is a schematic diagram which shows two internal helical protrusions caused by differential embedding and illustrates the helical spiral shape produced within the lumen of stent (10).

Figure 22:
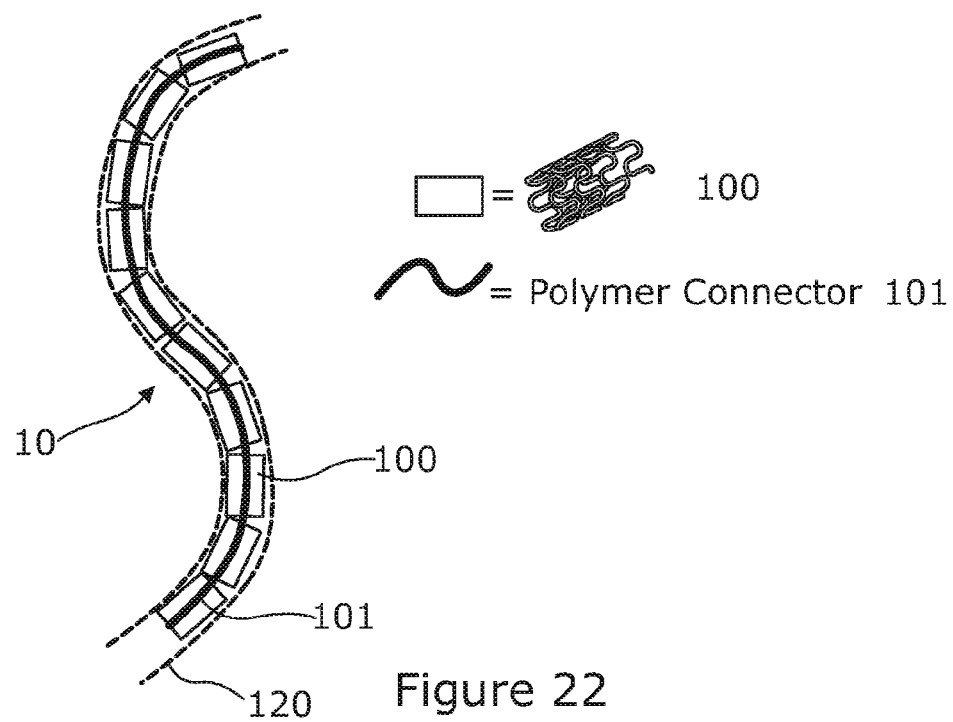
FIG. 22 illustrates a stent according to the invention comprising several short segments of tubular stent scaffolds linked together with a bioresorbable polymer to form a stent able to accommodate deployment within a tortuous vessel.

The tubular stent scaffold (100) would typically be formed to produce a tubular structure of 10 mm to 200 mm in length. In another embodiment, several segments of shorter tubular stent scaffolds (100) can be linked together with a bioresorbable polymer connector (101) to form longer stents with segments allowing for articulation to accommodate vessel (120) tortuosity similar to train cars following a curved track (FIG. 22).

In another embodiment, the stent scaffold (100) may contain one or more radiopaque markers (not illustrated) to improve in vivo visualization and to facilitate precise positioning of that part of the device. The radiopaque markers may be made from a biocompatible heavy metal such as gold, platinum or tantalum, or 316 SS for example. The marker may comprise a loop of radiopaque wire or a 'C' clip that also serves as additional end fixation.

In other embodiments, the radio-opacity may be achieved by loading all or some the printed bioresorbable polymer connector with a known biocompatible agent such barium carbonate or barium sulfate or iodinated compounds.

In other embodiments the stent of the present invention can be coated with a bioactive drug, for example having an antibacterial, anesthetic or anti-thrombotic activity. The stent can be coated with a 50-50 formulation of the drug (such as sirolimus, also known as rapamycin) in DL-PLA or PLGA polymer at a total dose of 5-10 µg/mm stent length and an elution time of 30 days or more. Other embodiments utilize analog 'limus drugs' such as Everolimus and Biolimus in similar doses. The coating of the bioactive drug can cover substantially the whole of the stent or substantially the whole of the stent scaffold, for example it may be convenient to apply the coating containing the bioactive drug prior to addition of the connector(s). Alternatively, the connectors can be added to the stent scaffold and the coating can then be applied to the whole stent. In certain embodiments the coating could be applied to selected portions of the stent or stent scaffold only, for example could be applied to the end portions of the device or to the middle section of the device. The coating can be a continuous layer or could be a discontinuous layer, i.e. need for cover every part of the device outer surface. The coating can be applied using routine coating methods, for example dip coating, spray coating, vapour deposition etc.

In another embodiment, the scaffold is coated with a paclitaxel-PLGA formulation (for example as described in EuroIntervention 8(12):1441-50, April 2013, the content of which is incorporated by reference).

Figure 23:
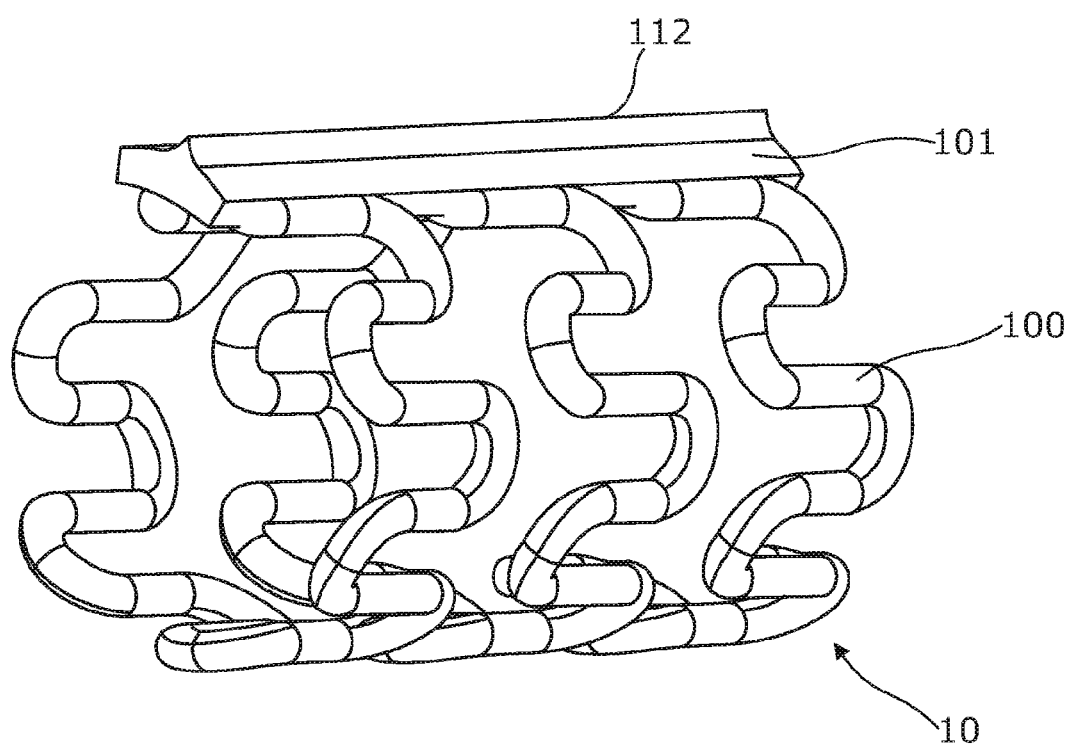
FIG. 23 shows a further embodiment of a stent according to the present invention in which the connector has a flanged outer edge.

In yet another embodiment, a fully bioresorbable stent scaffold (100) is provided that also provides the function of a 'cutting balloon'. Cutting balloons incorporate wire like blades that run longitudinally down the length of the balloon to cause a more controlled plane of dissection to the vessel intima during high pressure expansion. This is especially effective with so-called fibrous or highly calcified lesions that resist expansion and or suffer from high vessel recoil. The polymer connectors (101) can be micro-moulded to create a polymer fin (112) on the external surface of the connector that is approximately 50 to 250 microns tall (FIG. 23). In another embodiment, a similar effect is achieved by a segment of Mg based alloy wire of triangular cross-section that runs the full length of the stent on the external surface and is attached to the stent at the stent ends. In yet another embodiment, the wire can be platinum based to provide cutting action and also serve as a radiopaque marker.

In use, the bioresorbable stent (10) is crimped onto a balloon catheter, placed in a sterile barrier package and sterilized by EtO or other non-ionizing radiation method.

All documents referred to herein are incorporated by reference. Any modifications and/or variations to described embodiments that would be apparent to one of skill in art are hereby encompassed. Whilst the invention has been described herein with reference to certain specific embodiments and examples, it should be understood that the invention is not intended to be unduly limited to these specific embodiments or examples.

The invention claimed is:

1. A stent scaffold comprising a wire drawn from an alloy that consist:
   3.2 to 4.8% by weight lithium,
   0.5 to 2.0% by weight yttrium; and
   the balance being high purity magnesium, wherein said alloy has an Fe and Ca content of 150 ppm or less, and has less than 500 ppm of all other rare earth metals;
   wherein the wire is shaped into a repeating waveform having alternate crowns and troughs; and
   (1) the height of the repeating waveform is from 0.8 mm to 1.2 mm; or
   (2) the crowns of the repeating waveform in their formed position have an inner diameter, $D_{crown}$ according to the formula:

$$D_{crown} = X \times D_{wire}$$

wherein X is a ratio parameter having a value of from 2.4 to 2.8 and $D_{wire}$ is the cross-sectional diameter of the wire.

2. The stent scaffold as claimed in claim 1, wherein the repeating waveform is helically wound to form a tubular structure.

3. The stent scaffold as claimed in claim 1, wherein the repeating waveform includes at least three helical turns.

4. The stent scaffold as claimed in claim 1, wherein the crowns of the repeating waveform are aligned along a longitudinal axis of the stent scaffold.

5. The stent scaffold as claimed in claim 1, wherein the crowns of the repeating waveform are aligned in an anti-clockwise helix relative to a longitudinal axis of the stent scaffold.

6. The stent scaffold as claimed in claim 1, wherein the crowns of the repeating waveform are aligned in a clockwise helix relative to a longitudinal axis of the stent scaffold.

7. The stent scaffold as claimed in claim 1, wherein the repeating waveform consists of repeats of a unit waveform, each unit waveform having a first crown segment connected by a first leg to a trough which is connected to a second leg, the second leg being connected to a second crown segment and wherein the second crown segment connects to the first crown segment of the adjacent unit waveform to form a crown, and wherein the first leg have a different length to the second leg.

8. The stent scaffold as claimed in claim 1, wherein the repeating waveform consists of repeats of a unit waveform, each unit waveform having a first crown segment connected by a first leg to a trough which is connected to a second leg, the second leg being connected to a second crown segment and wherein the second crown segment connects to the first crown segment of the adjacent unit waveform to form a crown, and wherein the first leg is the same length as the second leg.

9. The stent scaffold as claimed in claim 1 which is at least partially coated with a layer of bioresorbable aliphatic polyester polymer.

10. The stent scaffold as claimed in claim 9 wherein said stent scaffold is coated at one or both ends with said layer of bioresorbable aliphatic polyester polymer.

11. The stent scaffold as claimed in claim 9 wherein said stent scaffold is substantially coated with said layer of bioresorbable aliphatic polyester polymer.

12. The stent scaffold as claimed in claim 9 wherein said layer of polymer is a conformal layer of aliphatic polyester polymer having a thickness of 20 microns or less.

13. The stent as claimed in claim 1 which further comprises a bioresorbable polymer connector which links at least two turns of the stent scaffold, wherein said bioresorbable polymer is an aliphatic polyester, and wherein said stent has a coating which comprises a bioactive drug.

14. A stent comprising:
   a stent scaffold comprises a wire drawn from an alloy that consist:
      3.2 to 4.8% by weight lithium,
      0.5 to 2.0% by weight yttrium; and
      the balance being high purity magnesium, wherein said alloy has an Fe and Ca content of 150 ppm or less, and has less than 500 ppm of all other rare earth metals;
   a first set of connectors, wherein the connector is a bioresorbable polymer connector that links at least two turns of the stent scaffold, and a longitudinal axis of each connector is aligned with a longitudinal axis of another connector within said first set, and wherein each connector has a length that is less than that of the stent scaffold; and a second set of connectors, with sets being spaced equi-distantly around the circumference of the stent scaffold.

15. The stent as claimed in claim 14 wherein the connector is attached to each turn of the scaffold along the full length of the stent scaffold.

16. The stent as claimed in claim 14, which comprises two, three or four connectors, and wherein the connectors are equi-distantly spaced from each other around the circumference of the stent scaffold.

17. The stent as claimed in claim 14, wherein the longitudinal axis of each connector is aligned with a longitudinal axis of the stent scaffold.

18. The stent as claimed in claim 14, wherein the longitudinal axis of each connector is angularly offset from a longitudinal axis of the stent scaffold.

19. The stent as claimed in claim 14 wherein the longitudinal axes of the connectors of the first set are aligned with the longitudinal axis of the stent scaffold.

20. The stent as claimed in claim 14 wherein the longitudinal axes of the connectors of the first set are angularly off-set from the longitudinal axis of the stent scaffold.

21. The stent as claimed in claim 14, wherein the longitudinal axis of each connector has the same helical angle as the longitudinal axis of another connector within said first set.

22. The stent as claimed in claim 14, further comprising a third sets of connectors, with each of the first, the second, and the third set being spaced equi-distantly around the circumference of the stent scaffold.

23. The stent as claimed in claim 14, wherein there is at least one connector at any cross-section along the length of the stent.

24. A stent comprising a stent scaffold and a bioresorbable polymer connector that links at least two turns of the stent scaffold, wherein:

the stent scaffold comprises a wire drawn from an alloy that consist:
3.2 to 4.8% by weight lithium,
0.5 to 2.0% by weight yttrium; and
the balance being high purity magnesium, wherein said alloy has an Fe and Ca content of 150 ppm or less, and has less than 500 ppm of all other rare earth metals; and wherein (1) at least one bioresorbable polymer connector is bonded to the stent scaffold such that the bioresorbable polymer connector partially envelops a strut of the stent scaffold such that the bioresorbable polymer connector at least partially uncouples from the stent scaffold during expansion of the stent in an angulated body lumen; or (2) at least one bioresorbable polymer connector has an external fin; or (3) the bioresorbable polymer connector(s) are helically arranged and wherein the width of the bioresorbable polymer connector(s) is 100% to 500% of the diameter of the wire, such that an internal spiral protrusion is formed within the lumen of the stent after deployment which causes spiral flow of fluid travelling therein.

25. The stent as claimed in claim 24 wherein the width of the at least one bioresorbable polymer connector is 100% to 500% of the diameter of the wire.

26. The stent as claimed in claim 24 having a coating which comprises a bioactive drug.

27. A stent comprising two or more stent scaffolds longitudinally connected together by a bioresorbable polymer connector; wherein said bioresorbable polymer connector is an amorphous copolymer of 20-30% glycolide and 70-80% lactide, and said polymer has a molecular weight greater than 70 k g/mol; and the stent scaffold comprising a wire drawn from an alloy that consist:
3.2 to 4.8% by weight lithium,
0.5 to 2.0% by weight yttrium; and
the balance being high purity magnesium, wherein said alloy has an Fe and Ca content of 150 ppm or less, and has less than 500 ppm of all other rare earth metals.

28. The stent as claimed in claim 27, wherein said bioresorbable polymer connector is a polyester.

29. The stent as claimed in claim 27, wherein said bioresorbable polymer connector is an aliphatic polyester.

30. The stent as claimed in claim 29, wherein said bioresorbable polymer connector is PLGA (poly(lactic-co-glycolic acid) or copolymers of PLGA or mixtures thereof.

31. The stent as claimed in claim 27, wherein there is always at least one bioresorbable polymer connector at any cross-section along the length of the stent.

\* \* \* \* \*